(12) United States Patent
Hane

(10) Patent No.: US 11,553,834 B2
(45) Date of Patent: Jan. 17, 2023

(54) FORCE ESTIMATION SYSTEM AND FORCE INFORMATION CALCULATION METHOD

(71) Applicant: OLYMPUS CORPORATION, Tokyo (JP)

(72) Inventor: Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 657 days.

(21) Appl. No.: 16/513,885

(22) Filed: Jul. 17, 2019

(65) Prior Publication Data

US 2019/0335981 A1 Nov. 7, 2019

Related U.S. Application Data

(63) Continuation of application No. PCT/JP2017/020991, filed on Jun. 6, 2017.

(51) Int. Cl.
*A61B 1/00* (2006.01)
*A61B 1/005* (2006.01)
*G01L 1/12* (2006.01)

(52) U.S. Cl.
CPC .......... *A61B 1/0057* (2013.01); *A61B 1/0011* (2013.01); *A61B 1/00147* (2013.01); *A61B 1/00165* (2013.01); *G01L 1/12* (2013.01)

(58) Field of Classification Search
None
See application file for complete search history.

(56) References Cited

U.S. PATENT DOCUMENTS

| 5,728,044 A * | 3/1998 | Shan .................. A61B 1/31 600/117 |
| 2002/0183592 A1* | 12/2002 | Suzuki .............. A61B 1/00098 600/117 |
| 2008/0221592 A1* | 9/2008 | Kawai ............... A61B 1/00042 606/130 |
| 2010/0030023 A1 | 2/2010 | Yoshie |
| 2011/0301414 A1* | 12/2011 | Hotto .................... A61B 5/145 600/114 |

(Continued)

FOREIGN PATENT DOCUMENTS

| CN | 101227854 A | 7/2008 |
| CN | 105025773 A | 11/2015 |

(Continued)

OTHER PUBLICATIONS

Chinese Office Action dated Sep. 26, 2021 received in 201780083694.1.

(Continued)

*Primary Examiner* — Timothy J Neal
(74) *Attorney, Agent, or Firm* — Scully, Scott, Murphy & Presser, P.C.

(57) ABSTRACT

A force estimation system for calculating force information regarding forces applied to one or more positions of a flexible tubular portion having flexibility through an arithmetic operation, the force estimation system comprising: a processor configured to input the deformation state and the mechanical property at a plurality of longitudinal positions of the flexible tubular portion, and calculates the force information of the force applied to the individual positions of the flexible tubular portion based on the deformed state and the mechanical property.

34 Claims, 24 Drawing Sheets

(56) References Cited

U.S. PATENT DOCUMENTS

| | | | |
|---|---|---|---|
| 2013/0261392 A1 | 10/2013 | Yamamoto et al. | |
| 2014/0100484 A1 | 4/2014 | Tsusaka et al. | |
| 2014/0230562 A1* | 8/2014 | Yamamoto | G01N 3/20 73/800 |
| 2015/0057575 A1* | 2/2015 | Tsusaka | A61M 25/0113 600/587 |
| 2015/0099926 A1* | 4/2015 | Davidson | A61B 1/00052 600/103 |
| 2015/0359419 A1 | 12/2015 | Hane et al. | |
| 2020/0253669 A1* | 8/2020 | Diolaiti | A61B 34/20 |

FOREIGN PATENT DOCUMENTS

| | | |
|---|---|---|
| JP | H 3-198828 A | 8/1991 |
| JP | 2009-522016 A | 6/2009 |
| JP | 2010-35768 A | 2/2010 |
| JP | 2012-115521 A | 6/2012 |
| JP | 2013-094337 A | 5/2013 |
| JP | 2014-95885 A | 5/2014 |
| JP | 2014-161374 A | 9/2014 |
| JP | 2015-16366 A | 1/2015 |
| JP | 2016-7434 A | 1/2016 |
| JP | 2017-623 A | 1/2017 |
| WO | WO 2016/189724 A1 | 12/2016 |

OTHER PUBLICATIONS

English translation of International Preliminary Report on Patentability dated Aug. 1, 2019, together with the Written Opinion received in related International Application No. PCT/JP2017/020991.

English translation of International Preliminary Report on Patentability dated Aug. 1, 2019, together with the Written Opinion received in related International Application No. PCT/JP2017/001431.

Chinese Office Action dated Apr. 8, 2021 received in 201780083694.1.

International Search Report dated Aug. 15, 2017 issued in PCT/JP2017/020991.

* cited by examiner

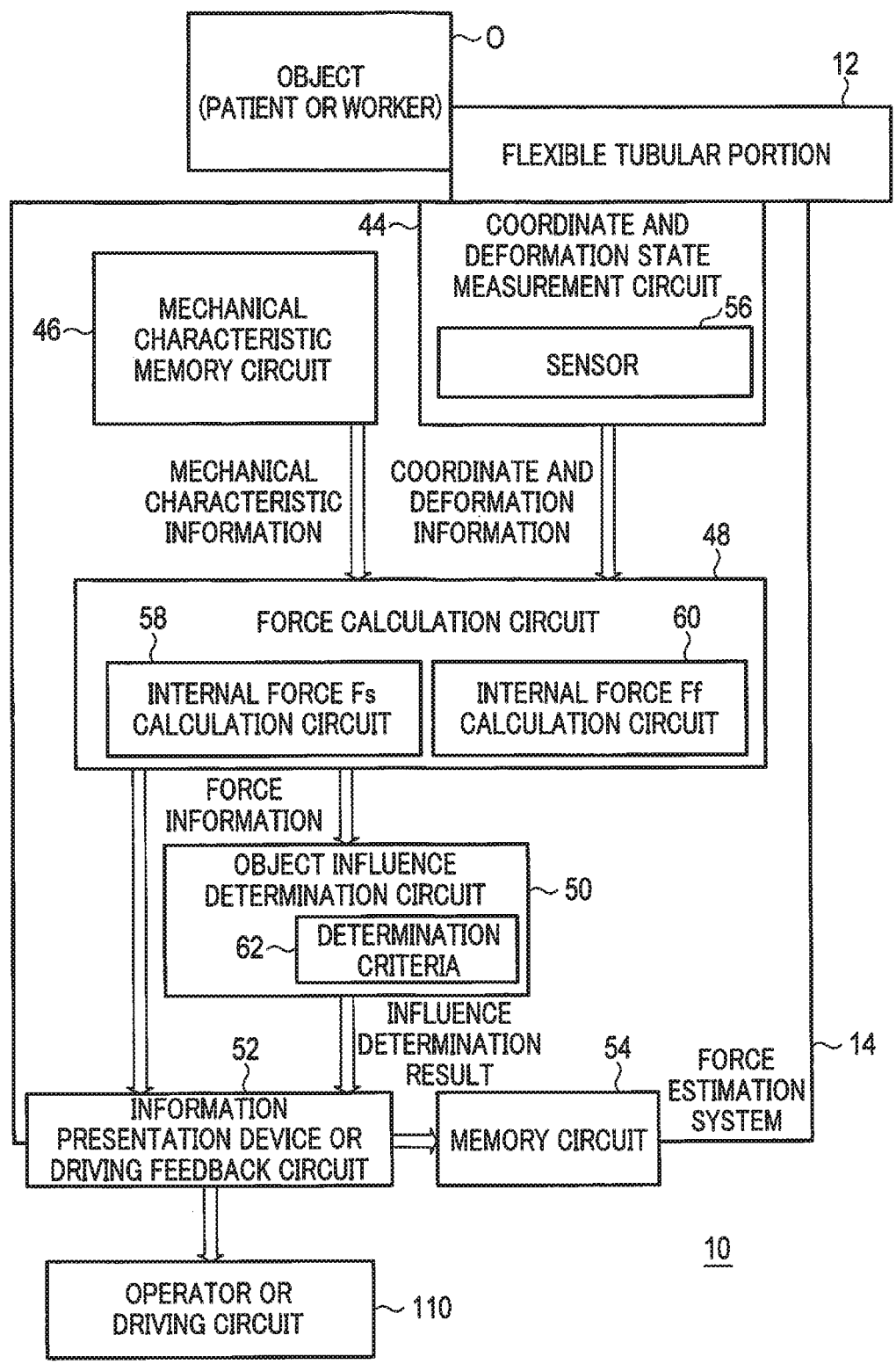
F I G. 1

LIGHT TRANSMISSION AMOUNT: MEDIUM

LIGHT TRANSMISSION AMOUNT: LARGE

LIGHT TRANSMISSION AMOUNT: SMALL

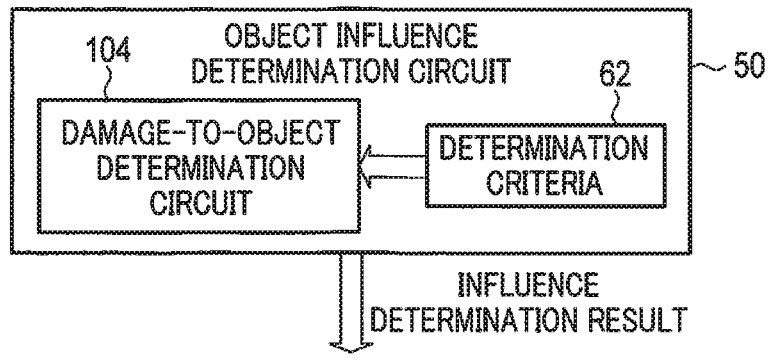
F I G. 19A
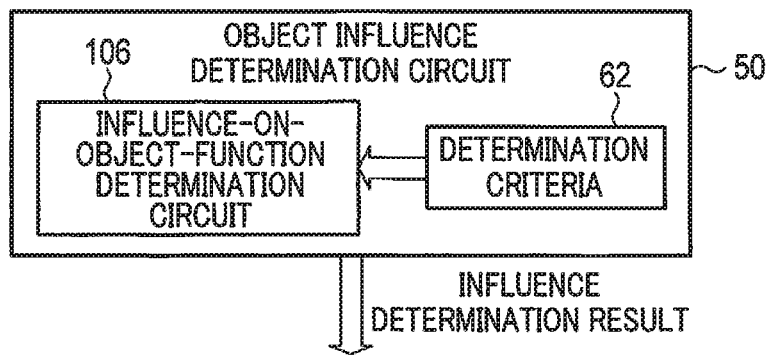
F I G. 19B
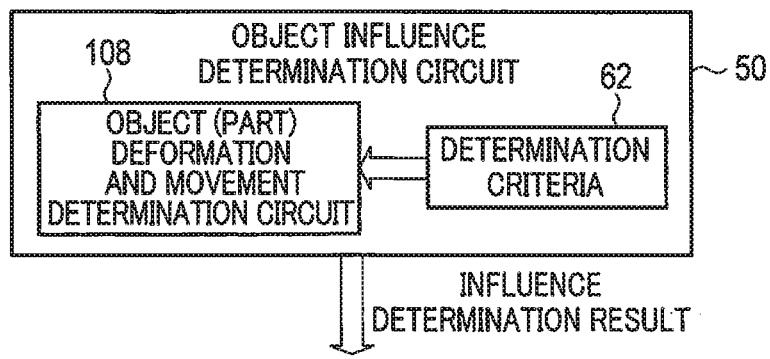
F I G. 19C

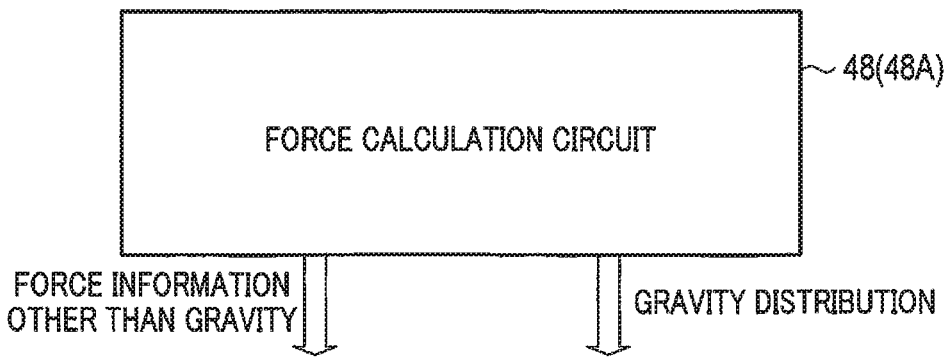
F I G. 27
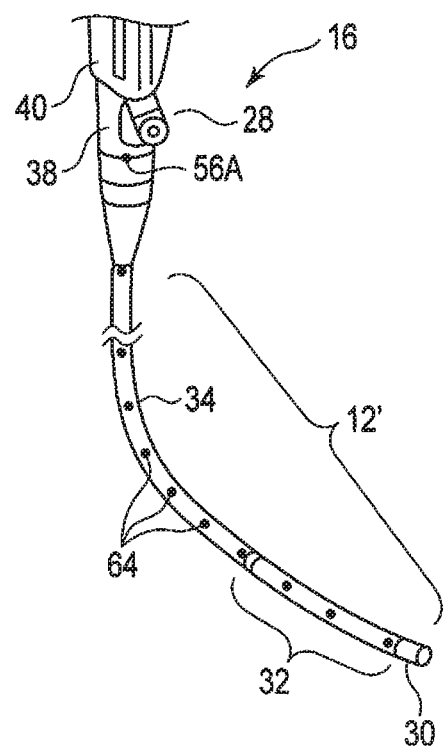
F I G. 28

FORCE ESTIMATION SYSTEM AND FORCE INFORMATION CALCULATION METHOD

CROSS-REFERENCE TO RELATED APPLICATIONS

This is a Continuation Application of PCT Application No. PCT/JP2017/020991, filed Jun. 6, 2017, and based upon and claiming the benefit of priority from prior PCT Application No. PCT/JP2017/001431, filed Jan. 17, 2017, the entire contents of all of which are incorporated herein by references.

FIELD

The embodiments of the present invention relates to a force estimation system and a force information calculation method. The variables in bold text, as used in the following description, denote a vector.

BACKGROUND

When an endoscope insertion portion is inserted into a body cavity of an object, or when a distal end of a medical manipulator contacts a body surface or organ of an object, there is an example in which a measurement unit that measures the amount of force received from the object is disposed at the endoscope insertion portion or the distal end of the medical manipulator. Such a measurement unit is, for example, a strain gauge (pressure-sensitive sensor).

An example of detecting the force by using such a pressure-sensitive sensor is disclosed in, for example, Patent Literature 1 (Jpn. PCT National Publication No. 2009-522016). In addition, an example of distributing and arranging a plurality of bending sensors in the flexible portion of the tubular insertion portion and calculating pieces of detection information of the plurality of bending sensors in combination through an arithmetic operation so as to extract manipulation support information including at least external force information about an external force applied to the tubular insertion portion is disclosed in, for example, Patent Literature 2 (Jpn. Pat. Appln. KOKAI Publication No. 2013-094337).

SUMMARY

According to an aspect of the present invention, a force estimation system comprising: a flexible tubular portion having flexibility; and a processor configured to calculate force information regarding forces applied to one or more positions of the flexible tubular portion through an arithmetic operation, and calculates the force information regarding the forces applied to the individual positions of the flexible tubular portion based on a deformation state and a mechanical characteristic at a plurality of longitudinal positions of the flexible tubular portion.

In addition, according to another aspect of the present invention, a force information calculation method for calculating force information regarding forces applied to one or more positions of a flexible tubular portion having flexibility, the force information calculation method comprising: a first step of measuring or estimating coordinates and shapes at a plurality of longitudinal positions of the flexible tubular portion; a second step of obtaining bending moments at the plurality of positions from the shapes obtained in the first step and a prestored bending stiffness at the plurality of positions; and a third step of calculating force information regarding the forces applied to the one or more positions of the flexible tubular portion from the coordinates of the plurality of positions obtained in the first step and the bending moments at the plurality of positions obtained in the second step.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram illustrating an overall configuration example of a force estimation system according to a first embodiment of the present invention.

FIG. 19A is a view illustrating a configuration example of an object influence determination unit in the case of determining a degree of damage to an object.

FIG. 19B is a view illustrating a configuration example of an object influence determination unit in the case of determining a degree of influence on an object function.

FIG. 19C is a view illustrating a configuration example of an object influence determination unit in the case of determining a degree of deformation and movement of an object.

FIG. 27 is a view illustrating a modified part from the configuration example of the force estimation system of FIG. 25 or FIG. 26 in the case of obtaining force information from which the influence of gravity is excluded.

FIG. 28 is a view illustrating an example of an endoscope in which a gravity sensor is incorporated in an operation portion.

DETAILED DESCRIPTION

Figure 2:
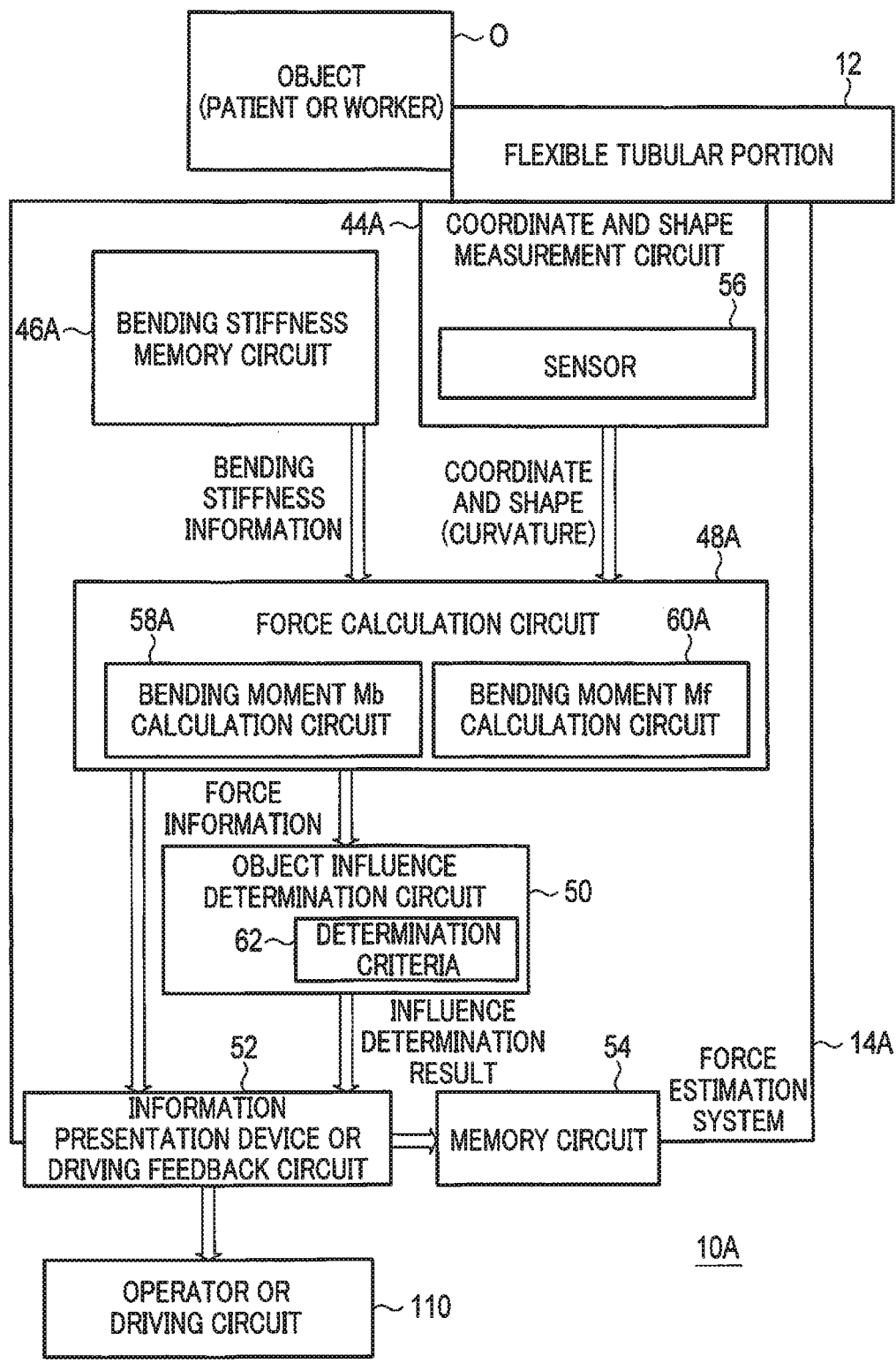
FIG. 2 is a block diagram illustrating a more specific overall configuration example of the force estimation system according to the first embodiment.

Hereinafter, embodiments of the present invention will be described in detail with reference to the drawin5gs.

Here, a force estimation system according to an embodiment will be described by taking the case of application to a medical endoscope as an example. However, it is apparent that the force estimation system according to the present invention can be applied universally as long as the force estimation system is an equipment that operates a flexible tubular portion so as to perform operations such as insertion or treatment. For example, in addition to medical endoscopes (an upper gastrointestinal endoscope, a large intestine endoscope, an ultrasound endoscope, a cystoscope, a nephroscope, and the like), the present invention can also be applied to devices having a thin flexible tubular portion such as a catheter, a medical manipulator, and an industrial endoscope.

First Embodiment

As illustrated in FIG. 1, an endoscope system that is a force estimation system 10 according to a first embodiment of the present invention has flexibility and includes an endoscope insertion portion that is a flexible tubular portion 12 inserted into a lumen of an object O. That is, in the present embodiment, it is mainly assumed that the flexible tubular portion 12 is inserted into the lumen of the object O, for example, a body cavity of a patient who is the object O, to perform operations such as diagnosis or treatment. The force estimation system 10 includes a force estimation system 14 that detects a force received from the body cavity by the flexible tubular portion 12, that is a force exerted on the body cavity side by the flexible tubular portion 12, during manipulation for insertion or operation of the flexible tubular portion 12, and calculates force information about forces applied to one or more positions of the flexible tubular portion 12 through an arithmetic operation. The force estimation system 10 can present the force information or the result of determining influence on the patient to an operator (workers of doctors) by using the calculated force information, and can provide feedback information to a driving system of the flexible tubular portion 12.

Here, the force information includes the position, direction, and magnitude of the force. The force estimation system 14 estimates an internal force to be applied to the flexible tubular portion 12 based on a deformation state and mechanical characteristics at a plurality of longitudinal positions of the flexible tubular portion 12, and calculates force information based on the estimated internal force. That is, the force estimation system 10 is a system that detects the force applied to the flexible tubular portion 12 based on a general internal force applied to the flexible tubular portion 12.

The internal force (force or moment) acting on a cross section of a structure is referred to as a sectional force. The sectional force includes an axial force, a shearing force, a bending moment, and a twisting moment.

FIG. 2 more specifically illustrates a force estimation system 10A that detects a force applied to a flexible tubular portion 12 based on a bending moment applied to the flexible tubular portion 12. In this case, a force estimation system 14A estimates a first bending moment applied to the flexible tubular portion 12 based on a shape and a bending stiffness at a plurality of longitudinal positions of the flexible tubular portion 12, and calculates force information based on the estimated first bending moment.

Hereinafter, each part will be described in more detail below.

[Object O and Lumen]

An object O assumes a patient to be diagnosed or treated or a patient's organ. A patient model or an organ model for simulation as a model may be used instead of the patient or the organ. As described above, it does not specialize in medical treatment, but may be a device, a work, or the like having a lumen or a hollow portion thereinside.

The object on which the operation is to be performed is not limited to the organ in the patient's body cavity. In a situation where deformation (bending or partial change in direction) of the flexible tubular portion is caused by an external force from the object O, the object may be the surface of the patient's body, the inside of the body opened by incision or the like, or the surface/inside of the human body model or the organ model, and may also be the surface or the inside of the object O such as a device or a structure by a manipulator or the like for inspection or repair.

The lumen of the object O, which is the target of the force estimation systems 10 and 10A according to the present embodiment, is a digestive organ, a bronchus, a urinary organ, or the like. In addition to the lumen, organs that are opened by surgery or the like are also the target. Here, a large intestine is taken as an example. The large intestine is an organ in which a shape, length, or arrangement is different depending on a person and a shape is particularly changed by the passage of time, insertion of a device, or the like.

[Endoscope System]

The force estimation systems 10 and 10A according to the present embodiment are applied to an endoscope system including an endoscope insertion portion that is the flexible tubular portion 12.

Figure 3:
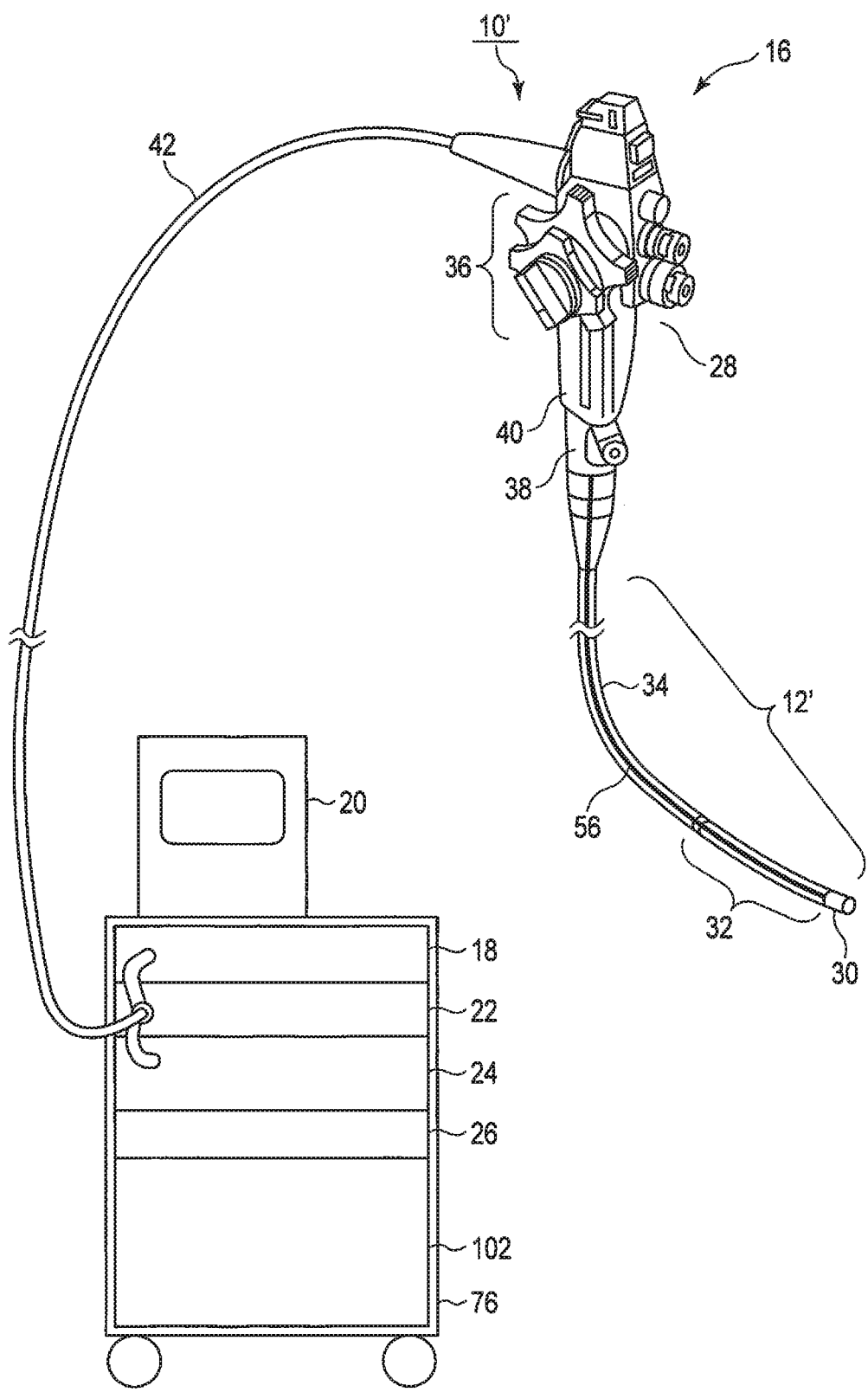
FIG. 3 is a view illustrating a configuration example of an endoscope system as an example of the force estimation system according to the first embodiment.

As illustrated in FIG. 3, the endoscope system 10' includes an endoscope 16 that captures an image of an observation object with an imaging unit provided at the distal end of the endoscope insertion portion, an image processing device 18 (video processor) that performs image processing on the image capturing result, and a monitor 20 that is a display unit connected to the image processing device 18 and displays the observation image that has been captured and image-processed. Here, the observation object is an affected part, a lesioned part, or the like in the object O (for example, the body cavity (lumen)).

In addition, the endoscope system 10' includes a light source device 22 that emits illumination light toward the endoscope 16, a light emission detection device 24 that emits light for detection of a shape sensor to be described later, which is different from illumination light, and detects the light, and a control device 26 that controls the endoscope system 10'.

The endoscope 16 is provided with an elongated endoscope insertion portion 12' that is the flexible tubular portion 12, and an operation portion 28 connected to a proximal end of the endoscope insertion portion 12'. The endoscope 16 is a tubular portion insertion device that inserts the tubular endoscope insertion portion 12' into the body cavity.

The endoscope insertion unit 12' includes a distal end hard portion 30, a bent portion 32, and a flexible tube portion 34 from a distal end side to a proximal end side of the endoscope insertion portion 12'. The proximal end of the distal end hard portion 30 is connected to the distal end of the bent portion 32, and the proximal end of the bent portion 32 is connected to the proximal end of the flexible tube portion 34.

The distal end hard portion 30 is the distal end of the endoscope insertion portion 12' and the distal end of the endoscope 16 and is hard, and the imaging unit is disposed therein.

The bent portion 32 is bent in a desired direction according to an operator's operation of a bending operation portion 36 provided in the operation portion 28. The bent portion 32 is bent to change the position and the direction of the distal end hard portion 30, the observation object is captured in the observation field of the imaging unit, and the observation object is illuminated with the illumination light. The bent portion 32 is configured by connecting joint rings (not illustrated) along the longitudinal direction of the endoscope insertion portion 12'.

The flexible tube portion 34 has desired flexibility and is bent by an external force. The flexible tube portion 34 is a tubular member extending from a main body portion 38 of the operation portion 28. Due to the flexibility, it is possible to insert the endoscope insertion portion 12' into the lumen of the patient who is the object O, such as a digestive organ, a bronchus, or a urinary organ, while bending or twisting the bent portion 32.

Figure 4:
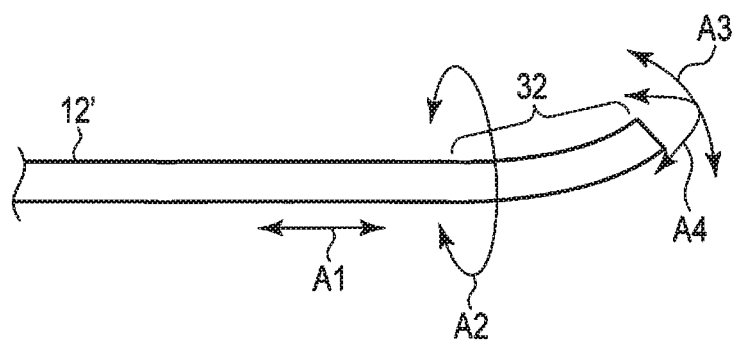
FIG. 4 is a view illustrating a main operation direction related to insertion and removal of an endoscope insertion portion.

Here, the main operation direction involved in the insertion and removal of the endoscope insertion portion 12' is an insertion and removal direction of the endoscope insertion portion 12' inserted into the lumen as indicated by a double-headed arrow A1 in FIG. 4 and a twisting (rotating) direction accompanied by the rotation of the operation portion 28 as indicated by a double-headed arrow A2. In addition, the main operation direction involved in the bending of the endoscope insertion portion 12' is a vertical direction of the bent portion 32 by the operation of the bending operation portion 36 as indicated by a double-headed arrow A3 and a horizontal direction of the bent portion 32 by the operation of the bending operation portion 36 as indicated by a double-headed arrow A4.

The operation portion 28 includes a main body portion 38 from which the flexible tube portion 34 extends, a grip portion 40 connected to the proximal end of the main body portion 38 and gripped by the operator who operates the endoscope 16, and a universal cord 42 connected to the grip portion 40. The bending operation portion 36 is disposed in the grip portion 40.

[Force Estimation Systems 14 and 14A] As illustrated in FIG. 1, the force estimation system 14 includes a coordinate and deformation state measurement circuit 44, a mechanical characteristic memory circuit 46, a force calculation circuit 48, an object influence determination circuit 50, an information presentation device or driving feedback circuit 52, and a memory circuit 54.

In addition, as illustrated in FIG. 2, the force estimation system 14A includes a coordinate and shape measurement circuit 44A, a bending stiffness memory circuit 46A, a force calculation circuit 48A, an object influence determination circuit 50, an information presentation device or driving feedback circuit 52, and a memory circuit 54.

Each of the coordinate and deformation state measurement circuit 44 and the coordinate and shape measurement circuit 44A has a sensor 56. In addition, the force calculation circuit 48 includes an internal force Fs calculation circuit 58 that calculates a first internal force Fs and an internal force Ff calculation circuit 60 that calculates a second internal force Ff, and the force calculation circuit 48A includes a bending moment Mb calculation circuit 58A that calculates a first bending moment Mb and a bending moment Mf calculation circuit 60A that calculates a second bending moment Mf. The object influence determination circuit 50 includes a determination criteria memory circuit 62.

[Sensor 56]

As illustrated in FIG. 3, the sensor 56 included in the coordinate and deformation state measurement circuit 44 or the coordinate and shape measurement circuit 44A is configured to detect positions (coordinates) and deformation states (stretching, bending, twisting, shape, and the like) at a plurality of positions of the endoscope insertion portion 12', which is the flexible tubular portion 12, in the longitudinal direction. The detected positions and deformation states may be displayed on the monitor 20.

The position information or the deformation state information are information obtained directly from the sensor 56 or information obtained by processing the information obtained from the sensor 56. In the latter case, an existing processing circuit or the like for processing the information obtained from the sensor 56 may be separately required, but a detailed description and illustration thereof are omitted. In addition, the processing circuit or the like can be incorporated in the coordinate and deformation state measurement circuit 44 and the coordinate and shape measurement circuit 44A.

As such a sensor 56, at least one of a position sensor 64 (see FIG. 5A) and a shape sensor 66 (see FIG. 5B) can be used. As the sensor 56 of the coordinate and deformation state measurement circuit 44, a twisting sensor that detects a twisting moment, a sensor that detects a stretching force, or the like can also be used.

When a plurality of position sensors 64 are arranged so as to be distributed in the endoscope insertion portion 12', a bent shape can also be detected by interpolating a plurality of detected positions.

In addition, as the shape sensor 66, the entire shape can be detected by arranging a plurality of bending sensors in the endoscope insertion portion 12'. If the position and the direction at a specific point of the endoscope insertion portion 12' can be determined, the positions of the respective portions of the endoscope insertion portion 12' can also be detected.

The position sensor 64 or the shape sensor 66 may be incorporated not only in the endoscope insertion portion 12' but also in an adjacent portion, for example, the operation portion 28. The operation portion 28 is also a portion adjacent to the endoscope insertion unit 12'. At this time, these sensors can detect the position and the shape of a portion including at least part of the endoscope insertion portion 12', for example, the endoscope insertion portion 12' and the operation portion 28.

In addition, these sensors may be incorporated in the endoscope insertion portion 12' or its periphery, and may obtain the position or shape at any time, or these sensors are detachable and may be attached only when it is desired to obtain the position or shape. As an example of attachment and detachment, a probe provided with these sensors is inserted into and removed from a forceps channel disposed inside the endoscope insertion portion 12'.

Furthermore, the position sensor 64 and the shape sensor 66 can be appropriately combined and arranged, whereby the position and the shape of the endoscope insertion portion 12' can be calculated.

Figure 5A:
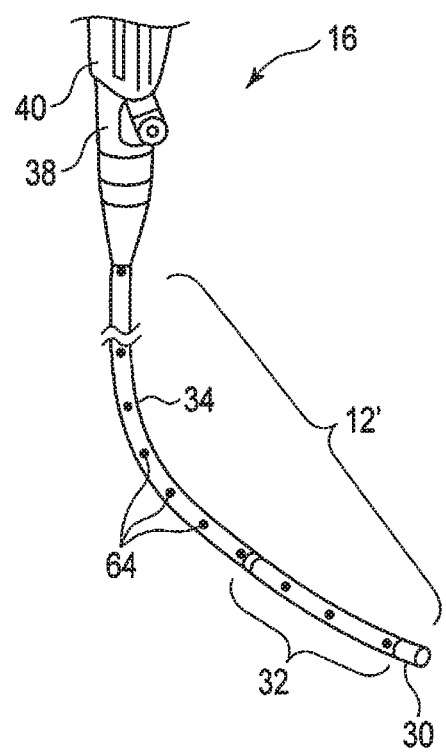
FIG. 5A is a view illustrating an example of an endoscope in which a position sensor is incorporated in an endoscope insertion portion.

FIG. 5A illustrates an example of the endoscope 16 in which a plurality of position sensors 64 arranged so as to be distributed in the endoscope insertion portion 12' are incorporated in the endoscope insertion portion 12'.

Figure 5B:
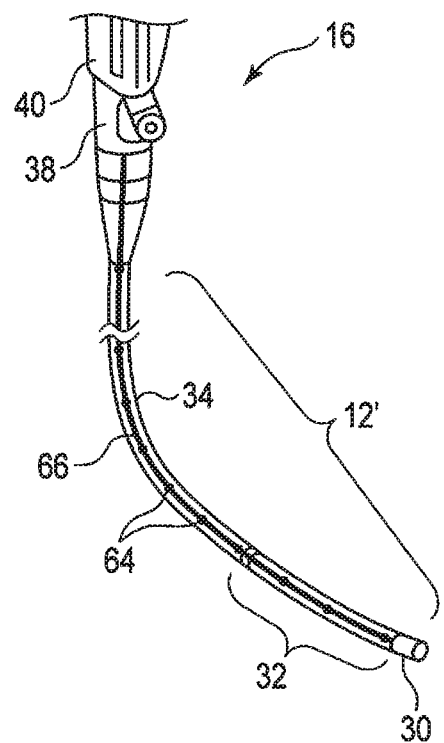
FIG. 5B is a view illustrating an example of an endoscope in which a position sensor and a shape sensor are incorporated in an endoscope insertion portion.

In addition, FIG. 5B illustrates an example of the endoscope 16 in which a plurality of position sensors 64 arranged so as to be distributed in the endoscope insertion portion 12' and a shape sensor 66 arranged along the longitudinal direction of the endoscope insertion portion 12' are incorporated in the endoscope insertion portion 12'.

The position sensors 64 and the shape sensor 66 can detect the shape and the arrangement of the endoscope insertion portion 12'. In addition, the shape sensor 66 can detect the curvature of each portion of the endoscope insertion portion 12'.

[Position Sensor 64]

The position sensor 64 can detect the (relative) position of the endoscope insertion portion 12' with respect to the object O or the place (the room or the like) where the object O is placed. For the position sensor 64, a magnetic position sensor, an ultrasonic position sensor, an optical position sensor, a position sensor using an acceleration sensor, and the like are known.

Figure 6:
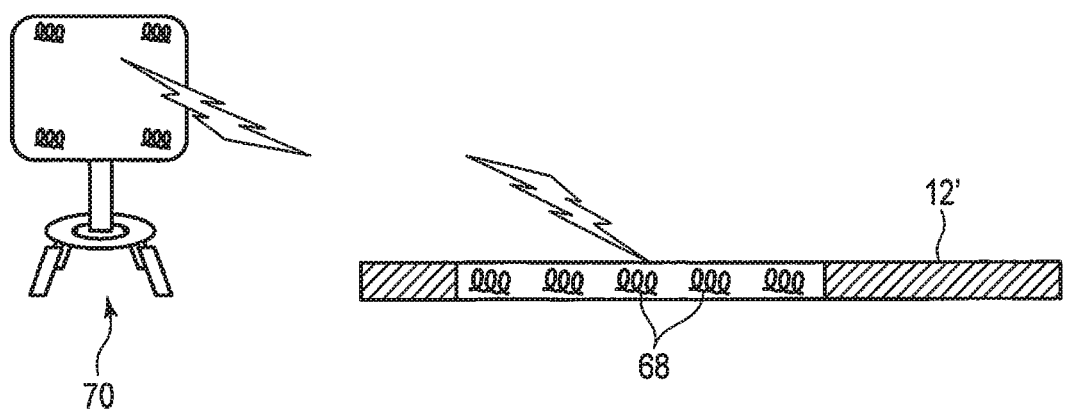
FIG. 6 is a view illustrating a configuration of a magnetic position sensor that detects a position of an endoscope insertion portion.

For example, as illustrated in FIG. 6, the magnetic position sensor 64 is constituted by a magnetic coil 68. The position sensor 64 using such a magnetic coil 68 is provided in the endoscope insertion portion 12', and one of a transmitter and a receiver is disposed in the room. In the example of FIG. 6, a magnetic antenna 70 is installed in the room. Therefore, the position of the endoscope insertion portion 12' in the room can be detected. If the magnetic antenna 70 is attached to the object O, the relative position of the endoscope insertion portion 12' with respect to the object O can be detected.

In addition, the magnetic position sensor 64 can also detect the direction. Therefore, not only the position but also the arrangement and posture of the endoscope insertion portion 12' can be detected by arranging a plurality of magnetic coils 68 at the same position in the longitudinal direction of the endoscope insertion portion 12' and at different positions in the circumferential direction.

Figure 7:
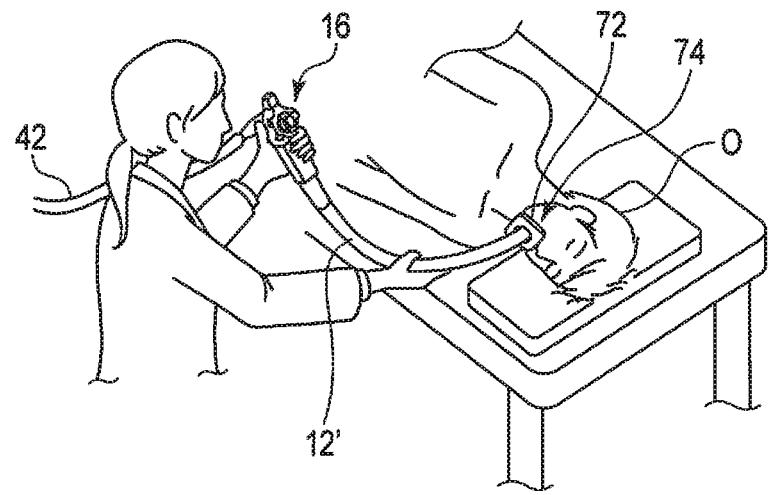
FIG. 7 is a view for explaining an insertion portion sensor disposed in an opening of a lumen of an object as another configuration example of a position sensor.

In addition, examples of the position sensor 64 that detects the relative position of the endoscope insertion portion 12' with respect to the object O may include an insertion portion sensor 72 as illustrated in FIG. 7. That is, the position of each part of the endoscope insertion portion 12' can also be detected by arranging the insertion portion sensor 72, which detects the insertion amount and rotation amount of the endoscope insertion portion 12', at an entrance 74 of a lumen of a patient who is the object O and combining the insertion portion sensor 72 with the shape sensor 66.

If the rear end of the shape sensor 66 is fixed to a fixed position, for example, an examination table in the room or a rack 76 (see FIG. 3) on which the image processing device 18 or the like is mounted, the insertion amount can be detected without using the insertion portion sensor 72.

[Shape Sensor 66]

As the shape sensor 66, a fiber sensor that is a bending sensor that detects bending from a curvature (bending amount) of a specific point by using an optical fiber is preferable. This fiber sensor is characterized in that (1) it has a small diameter and is easy to be incorporated in the endoscope 16 and (2) it is hardly affected by other configurations. Other configurations include incorporated components such as, for example, an operation wire disposed inside the endoscope insertion portion 12' for the bent portion 32.

Figure 8:
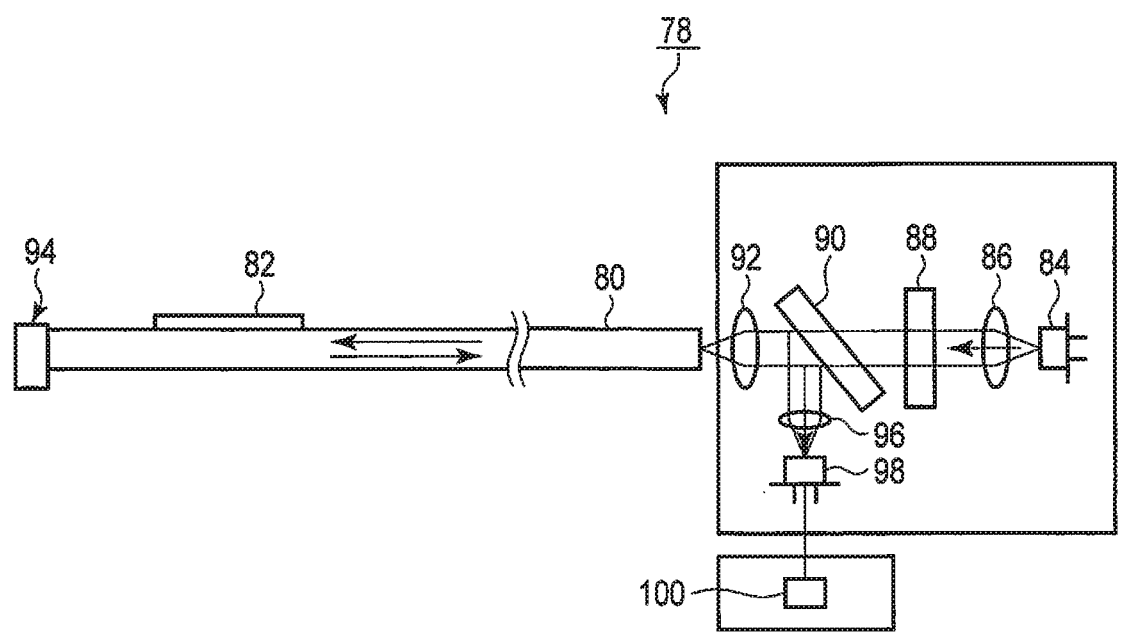
FIG. 8 is a view illustrating a configuration example of a shape sensor that detects a bent shape of an insert.

As illustrated in FIG. 8, the fiber sensor 78 is provided with an optical fiber 80 provided along the longitudinal direction of the endoscope insertion portion 12' and a detection target 82 at a specific point of the optical fiber 80, and detects the bent shape of the endoscope insertion portion 12' from the detected curvature.

Specifically, the fiber sensor 78 includes a light source 84 that is constituted by, for example, an LED and emits detection light having at least one wavelength different from the illumination light used in the endoscope 16. When a plurality of detection targets 82 are used, it is preferably configured to emit the detection light having a plurality of different wavelengths. The detection light emitted from the light source 84 is incident on the optical fiber 80 from the proximal end side of the optical fiber 80 through a projection lens 86, an isolator 88, a reflection mirror 90, and a first condensing lens 92.

The detection light guided by the optical fiber 80 is reflected by a reflecting portion 94 provided on the distal end side of the optical fiber 80, travels through the optical fiber 80 again as the detection light, and is emitted from the optical fiber 80.

The detection light emitted from the optical fiber 80 is transmitted through the first condensing lens 92, is bent and branched by the reflection mirror 90, and is received by a light detection unit 98 through a second condensing lens 96. The light detection unit 98 is constituted by a photoelectric conversion element or the like, and outputs a shape signal based on the light intensity of the detection light that changes due to the bending. A shape calculation unit 100 actually calculates and outputs the curvature of the bent shape of the endoscope insertion portion 12' based on the shape signal from the light detection unit 98.

Figure 9A:
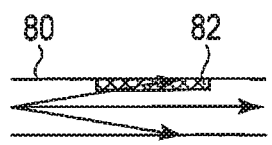
FIG. 9A is a view illustrating detection light guided in an optical fiber in a straight state.
Figure 9B:
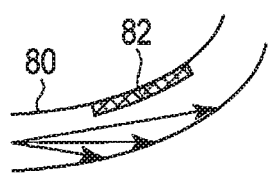
FIG. 9B is a view illustrating detection light guided in an optical fiber bent toward the side on which a detection target is formed.
Figure 9C:
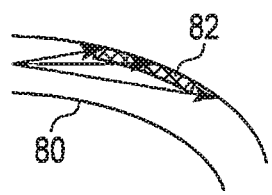
FIG. 9C is a view illustrating detection light guided in an optical fiber bent toward the side opposite to the side on which the detection target is formed.

The detection target 82 is attached to the outer circumferential surface of the specific point of the optical fiber 80, absorbs the guided detection light, and reduces light intensity, that is, reduces the light transmission amount. Therefore, the light transmission amount decreases as the amount of light irradiated to the detection target 82 increases. That is, when the optical fiber 80 changes from the straight state illustrated in FIG. 9A to any the bending state illustrated in FIG. 9B or FIG. 9C, a change in increase or decrease in the light transmission amount of the detection light occurs to synchronize. The change in the light transmission amount of the detection light is the change in the light intensity received by the light detection unit 98, and the shape calculation unit 100 can calculate the curvature of the optical fiber 80 from the bending direction of the detection target 82 and the detection signal based on the change in the light amount.

The fiber sensor 78 can detect the bending amount of the periphery by one detection target 82. The bending direction can also be detected by arranging a plurality of detection targets 82 in the axial rotating direction of the optical fiber 80. Furthermore, the bent shape can also be detected by arranging a plurality of detection targets 82 in the longitudinal direction of the optical fiber 80.

This system is a sensor suitable for mass-produced products because the detection unit can be configured inexpensively. Besides this, there is a system in which a grating is formed in an optical fiber called an FBG system. In this system, although the detection unit is complicated and expensive, a plurality of detection points can be provided on one optical fiber, and bending can be detected with high accuracy.

By using one or a plurality of fiber sensors 78 as the shape sensor 66, it is possible to provide a bending sensor that detects the bent shape of the endoscope insertion portion 12' in a desired range.

The shape sensor 66 is not limited to the fiber sensor 78, and may be any sensors as long as the sensors satisfy the function, size, and the like. For example, the shape of the flexible tubular portion 12 may be calculated from one or more camera images.

All or part of the components of the force estimation systems 14 and 14A excluding the sensor 56 as described above can be configured as a hardware circuit and accommodated in one housing and, as illustrated in FIG. 3, the housing 102 can be mounted on the rack 76 on which the control device 26 or the like of the endoscope system 10' is mounted. In addition, the hardware circuit that constitutes all or part of the components may be incorporated into the control device 26 of the endoscope system 10'. Furthermore, if desired results can be obtained, part of the components of the force estimation systems 14 and 14A excluding the sensor 56 may be disposed in the endoscope insertion portion 12' and/or in the operation portion 28.

Hereinafter, the components of the force estimation systems 14 and 14A excluding the sensor 56 will be described in more detail.

[Coordinate and Deformation State Measurement Circuit 44, Coordinate and Shape Measurement Circuit 44A]

The coordinate and deformation state measurement circuit 44 obtains the coordinate and deformation information of each portion of the endoscope insertion portion 12' from the detection result of the sensor 56, for example, at least one of the position sensor 64 and the shape sensor 66. In addition, the coordinate and shape measurement circuit 44A obtains the coordinates and the shape of each portion of the endoscope insertion portion 12' from the detection result of the sensor 56. When the information obtained directly from the sensor 56 is not the coordinate and deformation information or the shape, a process of processing the information obtained from the sensor 56 is also performed by the coordinate and deformation state measurement circuit 44 or the coordinate and shape measurement circuit 44A.

The coordinates are preferably coordinates of an inertial coordinate system, but in the case of a slow movement such as the human body under diagnosis or treatment, a coordinate system based on such a moving object may also be used.

The shape is preferably expressed by a curvature. The curvature represents the degree of bending at a specific point of the endoscope insertion portion 12', but may be represented by a specific range of bending amount, that is, a bending angle, instead of the curvature.

The coordinates and curvature may be replaced with other quantitative expressions, such as replacing the curvature with the bending amount, if it is possible to finally obtain the force information (position, direction, and magnitude of force) by performing processing to be described later.

Figure 10:
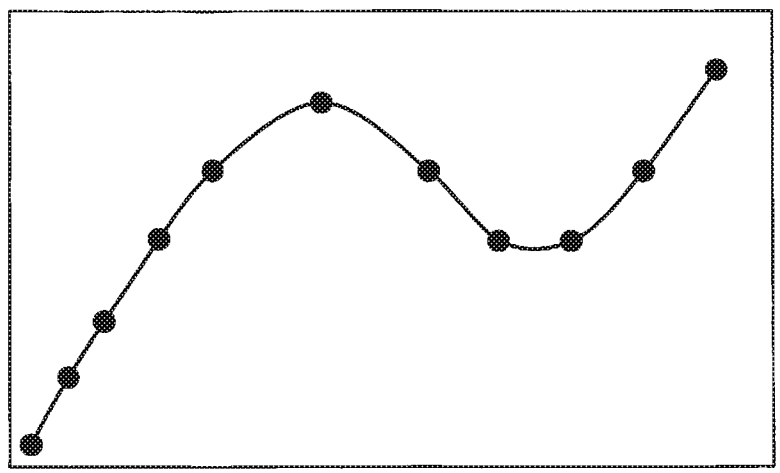
FIG. 10 is a view for explaining interpolation of coordinates or a shape.

Even if the coordinates and the shape cannot be obtained directly from the output of the mounted sensor 56, the necessary information is appropriately calculated by interpolating the position or the shape of each portion of the endoscope insertion portion 12'. For example, in FIG. 10, a plurality of dots represent the coordinates detected by the position sensor 64, and connecting these with a curve or the like is an example of interpolation. Similarly, if the shape is known and the coordinates of at least one dot are known, the coordinates and the shape at any position from that point can be obtained by calculation. As described above, the coordinates and the shape at any position of the endoscope insertion portion 12' can be obtained by appropriately performing interpolation or the like by using the information obtained from the sensor 56.

In addition, if a plurality of position sensors 64 are disposed in the endoscope insertion portion 12' as the sensor 56, a bent shape can also be detected by interpolating a plurality of detected positions.

In addition, the entire shape can be detected by arranging a plurality of shape sensors 66 (a plurality of bending sensors) in the endoscope insertion portion 12' as the sensor 56. If the position and the direction at a specific point of endoscope insertion part 12' are known, the positions of the respective portions of endoscope insertion portion 12' can also be detected.

Furthermore, the position sensor 64 and the shape sensor 66 can be appropriately combined and arranged, whereby the position and the shape of each portion of the endoscope insertion portion 12' can be calculated with high accuracy.

In addition, in order to perform processing of force calculation to be described later, it is preferable to (virtually) segment the endoscope insertion portion 12'. This processing is not essential for force calculation, but is introduced because it is useful for processing the force calculation and deepening the understanding of the force calculation.

Figure 11A:
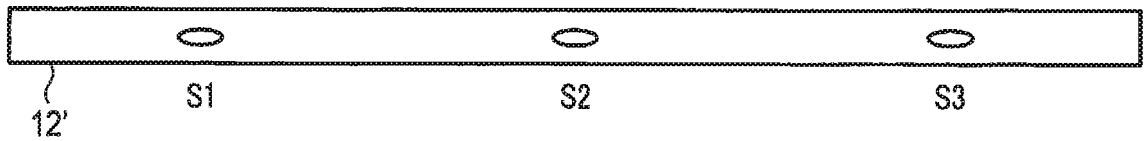
FIG. 11A is a view for explaining segment division and illustrates a state before division.

FIG. 11A illustrates an example of the endoscope insertion portion 12' in a straight state, and sensor detection points S1 to S3 represent examples of positions where the sensor 56 can directly detect at least one of the position (coordinates) and the curvature.

Figure 11B:
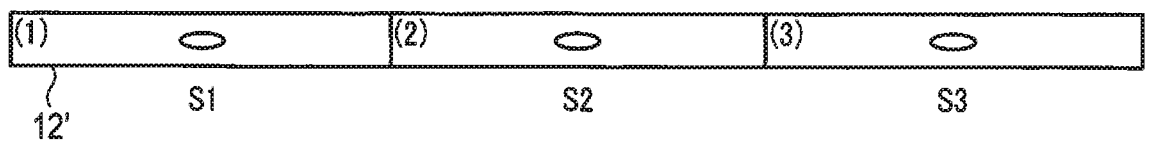
FIG. 11B is a view for explaining segment division and illustrates a segment division result in the case of being divided into three parts.

If the endoscope insertion portion 12' is divided into three segments of segment (1) to segment (3) according to the detection points S1 to S3 of the sensor 56, as illustrated in FIG. 11B, the positions and the curvatures of the segments (1) to (3) can be obtained. However, when the number of the detection points by the sensor 56 is small, the difference in curvature indicating the bent shape at the connection portion of each segment may be large, and the shape may not be smooth. In this case, the detection accuracy of the position or the shape may not be very high.

Figure 11C:
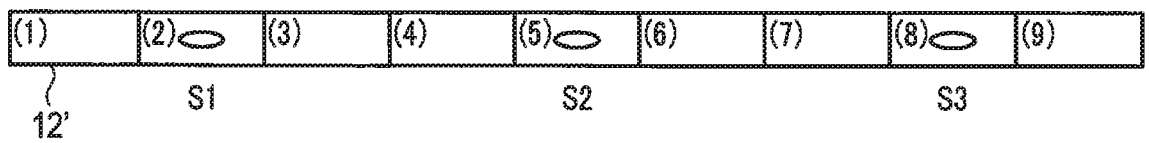
FIG. 11C is a view for explaining segment division and illustrates a segment division result in the case of being divided into nine parts.

Therefore, as illustrated in FIG. 11C, the endoscope insertion portion 12' is divided into smaller segments. The positions and the curvatures of the segments (1) to (9) can be obtained by interpolating the values at the detection points S1 to S3 of the sensor 56. By doing so, the difference in curvature which represents the bending shape at the connection portion of each segment decreases, and the position and the shape of the endoscope insertion portion 12' can be reproduced in a smooth manner, thereby increasing the position and shape detection accuracy.

In addition, a force application point to be described later may be designated by using finely divided segments.

The coordinate and deformation state measurement circuit 44 and the coordinate and shape measurement circuit 44A calculate coordinates and curvature corresponding to the segments.

The division method for determining the length or the like of the segment is assumed to correspond to the calculation accuracy required to calculate the force information and, when performing processing in real time, is assumed to correspond to the amount of calculation that can be processed so that the necessary processing is completed in a predetermined time. Furthermore, segment division does not necessarily need to be performed over the entire length of the endoscope insertion portion 12', and may be performed only in a necessary range. In addition, for the purpose of performing the minimum necessary processing, finely dividing a portion having a large curvature and roughly dividing a portion having a small curvature may be performed in real time.

It should be noted that the expression "the segment division is not essential" because the following description of each component, the calculation of coordinates and curvature, and the like are possible even if not divided virtually (that is, without introducing such a concept).

The following description will be given on the assumption that segment division has been performed.

[Mechanical Characteristic Memory Circuit 46, Bending Stiffness Memory Circuit 46A]

The mechanical characteristic memory circuit 46 is a semiconductor memory that stores the mechanical characteristic of each segment. Here, the mechanical characteristic is an index indicating the mechanical characteristic of each segment of the endoscope insertion portion 12'. For example, there are the Young's modulus or the mass of each segment, the magnitude of the twisting moment necessary to generate a certain twisting amount, the magnitude of a compression force or a tensile force necessary to perform certain expansion and contraction, and the like.

In addition, the bending stiffness memory circuit 46A is a semiconductor memory that stores the bending stiffness of each segment. The bending stiffness is an index indicating the bending difficulty of each segment of the endoscope insertion portion 12', which is one of the mechanical characteristics of each segment of the endoscope insertion portion 12'.

Such mechanical characteristics or the bending stiffness may be replaced with other quantitative expressions as long as the processing to be described later can be finally performed to obtain the force information.

In addition, it is not necessary to exactly store the mechanical characteristics or the bending stiffness of each segment, depending on the detection accuracy of the force. It may be represented by one value, or a number smaller than the number of segments may be stored. In addition, it may be an array or a function of values corresponding to the distance from the distal end or the proximal end of the endoscope insertion portion 12' instead of each segment.

Instead of providing the mechanical characteristic memory circuit 46 or the bending stiffness memory circuit 46A as an independent configuration, it may be particularly stored as a constant of processing content in a memory provided in the force calculation circuit 48 or 48A, details of which will be described later.

For the mechanical characteristic or the bending stiffness of each segment, a value can be set for each individual of the endoscope insertion portion 12'. In addition, since the value of the mechanical characteristic or the bending stiffness can be changed, the latest value corresponding to the temporal change of the endoscope insertion portion 12' can be used in the force calculation circuits 48 and 48A.

[Force Calculation Circuits 48 and 48A]

The force calculation circuit 48 calculates force information (force information) about the forces applied to one or more positions in the longitudinal direction of the endoscope insertion portion 12' based on the coordinate and deformation information of each segment, which is measured, calculated, and output by the coordinate and deformation state measurement circuit 44, and the mechanical characteristic information of each segment, which is output from the mechanical characteristic memory circuit 46.

The force calculation circuit 48A calculates force information about the forces applied to one or more positions in the longitudinal direction of the endoscope insertion portion 12' based on the coordinates and the shape of each segment, which are measured, calculated, and output by the coordinate and shape measurement circuit 44A, and the bending stiffness information of each segment, which is output from the bending stiffness memory circuit 46A.

The force information is at least one or more pieces of information about the position to which the force is applied, the direction of the force, and the magnitude of the force. If there is a known position, direction, and magnitude of the force information, it may be excluded from the force information. In addition, unnecessary information, for example, information not to be presented to the operator or the like may be excluded.

The calculation of the force information is performed based on a dynamic principle.

An example based on the following conditions is shown as an example of calculation of force information.

Force calculation circuit 48: In each segment, "first internal force Fs estimated from deformation state" and "second internal force Ff estimated from externally applied force" are substantially the same (detection principle 1A).

Force calculation circuit 48A: In each segment, "first bending moment Mb estimated from shape" and "second bending moment Mf estimated from externally applied force" are substantially the same (detection principle 1B).

These are based on static balance, and it is assumed that the movement of the endoscope insertion portion 12' or the object O is loose. In insertion, diagnosis, or treatment with the endoscope 16 or the medical manipulator, since the movement is generally loose, high accuracy results are expected.

For the calculation of the force information, the dynamic principle other than the static force balance may be used, or a combination of the static force balance and other dynamic principles may be used. In addition, a formula obtained by changing the method of physical expression, which is obtained by modifying Formula 6 of the static force balance shown below, may be used.

The force calculation circuit 48 includes the internal force Fs calculation circuit 58 and the internal force Ff calculation circuit 60 as described above. In the calculation of the force information based on the static balance, for each segment, the first internal force Fs estimated from the deformation state is calculated by the internal force Fs calculation circuit 58, and the second internal force Ff estimated from the force applied from the outside is calculated by the internal force Ff calculation circuit 60. Due to this, the conditional expression that the first internal force Fs and the second internal force Ff are substantially the same can be the number $N_s$ of segments in the case of two-dimension. (The number of conditional expressions can be, for example, $3N_s$ in the case of three-dimension.) Similarly, as described above, the force calculation circuit 48A includes the bending moment Mb calculation circuit 58A and the bending moment Mf calculation circuit 60A. In the calculation of the force information based on the static balance, for each segment, the first bending moment Mb estimated from the shape is calculated by the bending moment Mb calculation circuit 58A, and the second bending moment Mf estimated from the externally applied force is calculated by the bending moment Mf calculation circuit 60A. Due to this, the conditional formula that the first bending moment Mb and the second bending moment Mf are substantially the same can be the number $N_s$ of segments in the case of two-dimension. (The number of conditional expressions can be, for example, $3N_s$ in the case of three-dimension.) On the other hand, in the force information to be calculated, there are only $N_f \times N_c$ variables, which are the product of the number $N_f$ of forces and the number of information contents $N_c$.

When the following is established, the value of the variable can be uniquely obtained.

number of conditional expressions ($N_s$ or $3N_s$)=number of variables ($N_f \times N_c$).

In addition, when the following is established, the value of the variable cannot be uniquely obtained, and a combination of solutions of variables considered to be appropriate is obtained. Usually, a combination of solutions is obtained by an optimization method that minimizes or maximizes a particular evaluation formula.

$$\text{number of conditional expressions}(N_s \text{ or } 3N_s) > \text{number of variables}(N_f \times N_c).$$

In the case of the three-dimension, the number of information contents $N_c$ to be obtained, which affects the number of variables, can be $N_c=3$ if there is no particular limitation, as in force magnitude 1 and direction 2 or force component 3.

Figure 12:
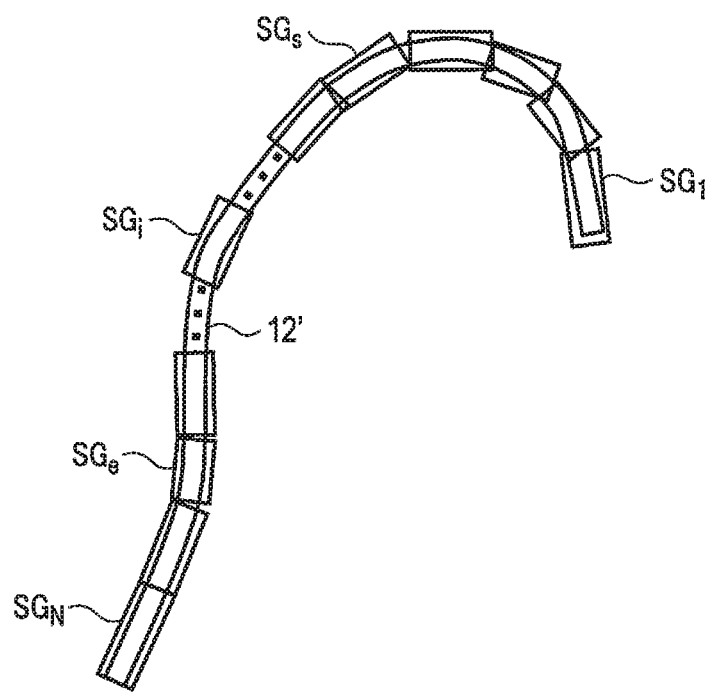
FIG. 12 is a view illustrating an endoscope insertion portion divided into segments.

FIG. 12 illustrates the endoscope insertion portion 12' of the endoscope 16 divided into segments. In FIG. 12, there are N segments from the segment $SG_1$ on the distal end side of the endoscope insertion portion 12' to the segment $SG_N$ on the proximal side. Among these, $N_s$ segments from segment $SG_s$ to segment $SG_e$ are objects to be calculated.

Hereinafter, the internal force Fs calculation circuit 58 and the bending moment Mb calculation circuit 58A, the internal force Ff calculation circuit 60 and the bending moment Mf calculation circuit 60A, and the optimization method will be described in detail.

[Internal Force Fs Calculation Circuit 58]

The internal force Fs calculation circuit 58 obtains (estimates) the first internal force Fs from the mechanical characteristic and the deformation state in each segment of the endoscope insertion portion 12'. As the internal force, as described above, there are an axial force, a shearing force, a bending moment, and a twisting moment, and a value is obtained for one or more of them.

For example, one or more deformations corresponding to an axial force, a bending moment, or a twisting moment, which is a tensile force or a compressive force in the longitudinal direction of the endoscope insertion portion 12', are obtained. In order to obtain the deformation amounts, sensors that obtain the stretching amount, the bending amount, and/or the twisting amount may be provided. It is generally known that if there are a plurality of position sensors 64, it is possible to obtain the stretching amount and the bending amount, and if a plurality of strain sensors are appropriately combined and used, the stretching amount, the bending amount, and the twisting amount can be obtained.

If the system has the magnitude of the internal force necessary to cause a predetermined amount of deformation as the mechanical characteristic, the axial force, the bending moment, and/or the twisting moment can be obtained from the stretching amount, the bending amount, and/or the twisting amount and the mechanical characteristic.

The internal force Fs calculation circuit 58 will be described in detail below as the bending moment Mb calculation circuit 58A, taking the bending moment as an example.

[Bending Moment Mb Calculation Circuit 58A]

The bending moment Mb calculation circuit 58A obtains (estimates) the first bending moment Mb from the bending stiffness and the bent shape in each segment of the endoscope insertion portion 12'.

A specific calculation will be described in the two-dimensional case for simplification.

Examples that can be simplified in two-dimension include a case where the object O or a member disposed around the object O has a portion generally parallel to a horizontal plane and the endoscope insertion portion 12' moves parallel to the portion, or furthermore, a case where the endoscope insertion portion 12' can support its own weight and maintain its posture, and a force is applied from the horizontal direction, or the magnitude of gravity can be ignored compared to the magnitude of the force from the horizontal direction.

Each segment is straight if no bending moment is applied. However, the portion of the bent portion 32 of the endoscope insertion portion 12' can be bent by the bending operation, and the shape may not be straight when there is no bending moment due to an external force. Therefore, with respect to the portion of the bent portion 32, the first bending moment Mb is obtained based on a change from this state based on the state in which no external force is applied. For the sake of simplicity, the bent portion 32 may be excluded from the segment to be calculated.

Figure 13:
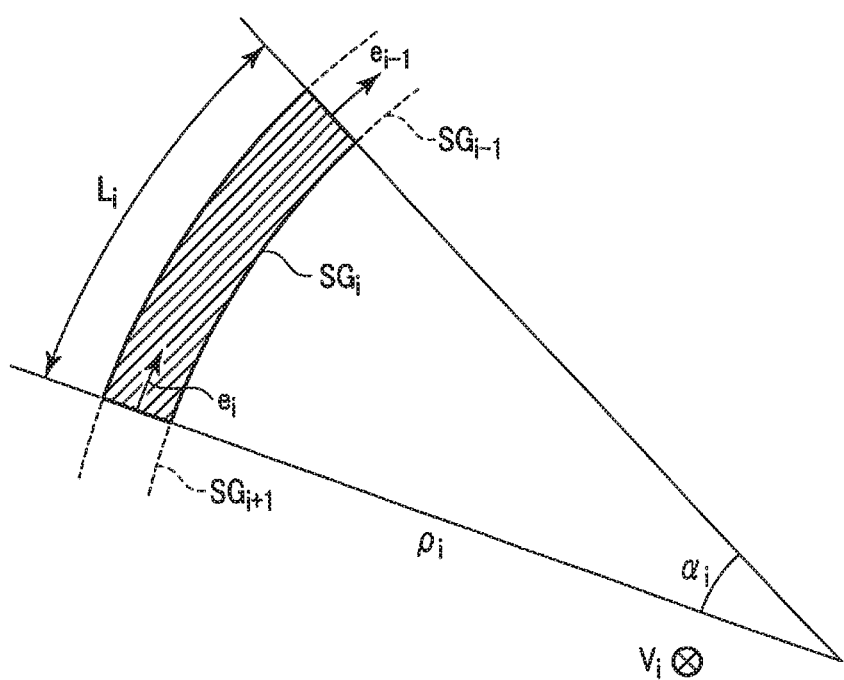
FIG. 13 is a view illustrating a bent shape of a segment $SG_i$.

The bent shape of the i-th segment $SG_i$ is illustrated in FIG. 13. The shape of the segment $SG_i$ is approximated to a circular arc.

Here, the definition is made as follows. In the following, "i" is a subscript corresponding to the segment $SG_i$.

Bending moment estimated from shape: $Mb_i$
Young's modulus: $E_i$
Moment of inertia of are: $I_i$
Direction vector of segment $SG_i$: $e_i$ Here, the direction vector $e_i$ is a direction vector at the connection portion of the segment $SG_{i+1}$ and the segment $SG_i$ and is directed toward the segment $SG_{i-1}$.

Direction vector perpendicular to paper: $V_i$
Curvature: $\chi_i$ (=1/$\rho_i$)

Here, $\rho i$ is a radius of curvature.
Bending stiffness: $G_i$ (=$E_i \cdot I_i$).

At this time, the following is established from the material dynamics for an arbitrary segment $SG_i$.

$$Mb_i = E_i/\rho_i \cdot I_i \quad \text{(Formula 1)}$$

$$\alpha_i = L_i/\rho_i \quad \text{(Formula 2)}$$

Here, $\alpha_i$ is an angle [rad].
From Formula 2, $$\begin{aligned} Mb_i &= (\alpha_i/L_i) \cdot (E_i \cdot I_i) \\ &= \chi_i \cdot G_i \end{aligned} \quad \text{(Formula 3)}$$

Here, "$E_i \cdot I_i = G_i$" is referred to as bending stiffness.

From Formula 3, the first bending moment Mb in the segment $SG_i$, which is estimated from the bent shape, is obtained.

Strictly speaking, the bending stiffness Gi changes with the magnitude of the curvature $\chi_i$, but often does not change significantly. Therefore, the bending stiffness $G_i$ may be treated as a constant, or may be regarded as a variable of the curvature $\chi_i$ if strictness is required.

In two-dimension, when the segment $SG_{i-1}$ side near the distal end of the endoscope insertion portion 12' is bent counterclockwise, the bending moment $Mb_i > 0$ and the angle $\alpha_i > 0$.

In the case of the three-dimension, the bending direction can be any of the following.

(1) Direction of bending around a direction perpendicular to the paper surface (2) Direction perpendicular to both the direction vectors $e_i$ and $V_i$.

At this time, the bending moment $Mb_i$ is expressed as a combination of a scalar and the above-described direction, or as a vector.

[Internal Force Ff Calculation Circuit 60]

The internal force Ff calculation circuit 60 obtains (estimates) the second internal force Ff that is a force applied to the endoscope insertion portion 12', which generates the first internal force Fs in each segment of the endoscope insertion portion 12'. As the first internal force Fs, the force calculated by the internal force Fs calculation circuit 58 is used.

The first internal force Fs obtained by the internal force Fs calculation circuit 58 includes, for example, an axial force, a bending moment, a twisting moment, or a combination thereof. The internal force Ff calculation circuit 60 obtains the second internal force Ff, which is a force that generates all the internal forces obtained by the internal force Fs calculation circuit 58, by using one or more segments.

The internal force Ff calculation circuit 60 will be described in detail below as the bending moment Mf calculation circuit 60A, taking the bending moment as an example.

[Bending Moment Mf Calculation Circuit 60A]

The bending moment Mf calculation circuit 60A obtains (estimates) the second bending moment Mf by an externally applied force, which is generated in each segment of the endoscope insertion portion 12'.

Regarding a specific calculation, for simplicity, a case where one force acts on the endoscope insertion portion 12' will be described.

Figure 14:
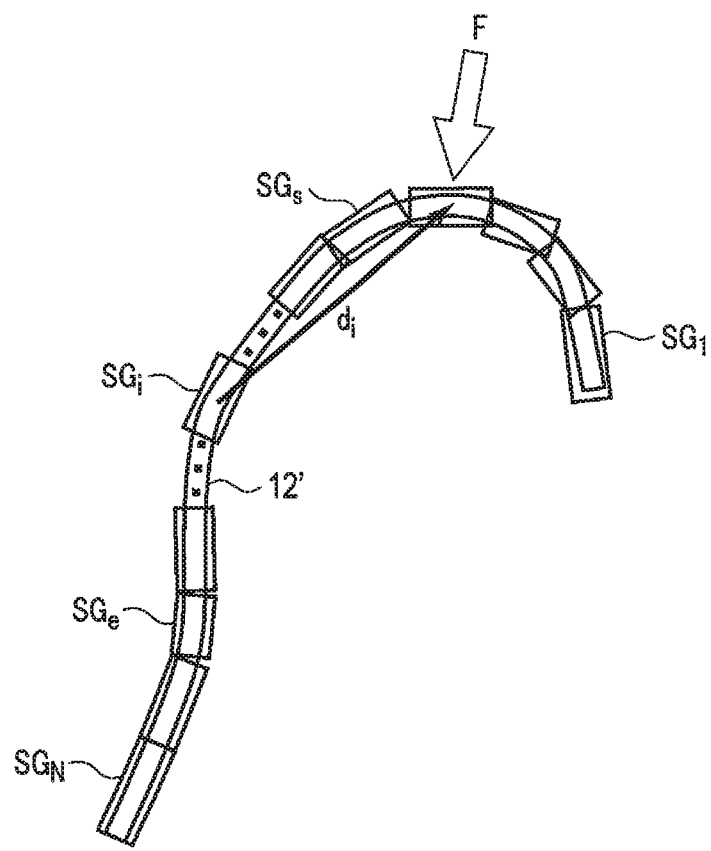
FIG. 14 is a view illustrating a pressing force F applied to an endoscope insertion portion and a vector $d_i$ from a center of a segment $SG_i$ to a position to which the pressing force F is applied.

In FIG. 14, the second bending moment $Mf_i$ applied to the segment $SG_i$ by the external force is as follows in mechanics.

«Case of Two-Dimension (X and Y Coordinates)»

When the position at which the pressing force F (vector) is applied is more distal than the position of the segment $SG_i$, the second bending moment $Mf_i$ is as follows. The second bending moment $Mf_i$ is a scalar and is a value+in the case of a counterclockwise bending moment.

$Mf_i = z$ component of $(d_i \times F)$ (Formula 4a)

Here,
"×": cross product
$d_i$: Vector from the center of segment $SG_i$ to the position at which pressing force F is applied.
The second bending moment $Mf_i$ may be $Mf_i = |d_i \times F|$ (absolute value).

In addition, when the application position of the pressing force F is nearer to the proximal side than the position of the segment $SG_i$, the second bending moment $Mf_i$ is as follows:

$Mf_i = 0$(scalar) (Formula 4b)

«Case of Three-Dimension»

When the position at which the pressing force F (vector) is applied is more distal than the position of the segment $SG_i$, the second bending moment $Mf_i$ is as follows. The second bending moment $Mf_i$ is a vector.

$Mf_i = d_i \times F$ (Formula 4c)

In addition, when the application position of the pressing force F is nearer to the proximal side than the position of the segment $SG_i$, the second bending moment $Mf_i$ is as follows:

$Mf_i = 0$(0 vector) (Formula 4d)

The 0 vector is a vector of size 0.

Next, a case where a plurality of forces act on the endoscope insertion portion 12' will be described.

In this case, the combined force of a plurality of forces may be calculated for the pressing force $F_j$ at which the position to which the force is applied is more distal than the position of the segment $SG_i$.

When the force is a distributed load, as described later, it may be regarded as being concentrated at a specific plurality of points.

«Case of Two-Dimension (X and Y Coordinates)»

In this case, the second bending moment $Mf_i$ is as follows.

$Mf_i = z$ component of $[\Sigma(d_{ij} \times F_j)]$,

However, only the force on the side more distal than the position of the segment $SG_i$ is calculated.
(Formula 5a)
Here,
$F_j$: external force (vector),
"×": cross product.
The second bending moment $Mf_i$ may be $Mf_i = |\Sigma(d_{ij} \times F_i)|$ (absolute value).

«Case of Three-Dimension»

In this case, the second bending moment $Mf_i$ is as follows.

$Mf_i = \Sigma(d_{ij} \times F_j)$

However, only the force on the side more distal than the position of the segment $SG_i$ is calculated.
(Formula 5b)

[Application of Optimization Method]

The force calculation circuit 48A calculates at least a necessary one of position, direction, and magnitude, which are force information, based on Formula 6 below.

$Mf_i \approx Mb_i$ (Formula 6)

When the number of conditional expressions ($N_s$) is larger than the number of variables ($N_j \times N_c$), a combination of solutions is obtained by an optimization method that minimizes or maximizes a particular evaluation formula.

An example in which one force is applied in two-dimension (within XY coordinates) will be described.

The position in the longitudinal direction is used as the position at which the force is applied, and the direction with respect to the central axis (direction around axis, that is, angle with respect to axis) is used as the direction of the force. In addition, an example of an evaluation formula for applying the optimization method is shown in Formula 7 below.

$\Sigma(Mf_i - Mb_i)^2$ Evaluation formula $i = s \sim e$ i.e. ranging from $s$ to $e$ (Formula 7)

The force calculation circuit 48A obtains a solution of a variable that minimizes Formula 7 by the optimization method.

The evaluation formula may use a suitable formula, as appropriate, such as a formula in which each segment is weighted.

In the optimization method that deal with multiple variables, various methods such as collective descent methods represented by differential evolution and particle swarm optimization, genetic algorithm, and the like have been proposed in recent years. The optimization method applied to the present embodiment may be any method as long as mathematical expressions that handle forces including multiple variables can be processed and the accuracy and convergence speed are sufficient for real-time processing. Therefore, it is sufficient to select an appropriate method in accordance with Formula 7 that is the evaluation formula.

In addition, when the evaluation formula can be simplified and expressed in the form of a polynomial, the least square method may be adopted.

[Minimization of Number of Variables]

The number of variables is preferably as small as possible. This is to make it possible to solve the variable, or to reduce the processing amount and processing time of the calculation for obtaining the variable.

In order to reduce the number of parameters, the position in the longitudinal direction is used as the position at which the force is applied, and the direction with respect to the central axis (direction around axis, angle with respect to axis) is used as the direction of the force.

Furthermore, the parameters may be reduced as appropriate. For example, if it can be regarded as two-dimension, the direction around the axis is not necessary. In addition, when a friction force is extremely small, the angle with respect to the axis may be regarded as perpendicular.

[Simplification of Force Information]

In order to make the position at which the force is applied limited and discrete, one or a plurality of fixed positions at which the force is applied may be prepared to reduce the amount of calculation processing.

As an example of a simplified model in which the position at which the force is applied is limited and discrete, there is a following example.

Consider load distribution as a force applied to a finite point.
Limit a force application direction to two-dimension.
The force shall be applied perpendicularly to the flexible tubular portion 12. (That is, the friction force is zero.)

When a plurality of forces act in the circumferential direction (around the central axis), only one of these combined forces is applied.

Figure 15:
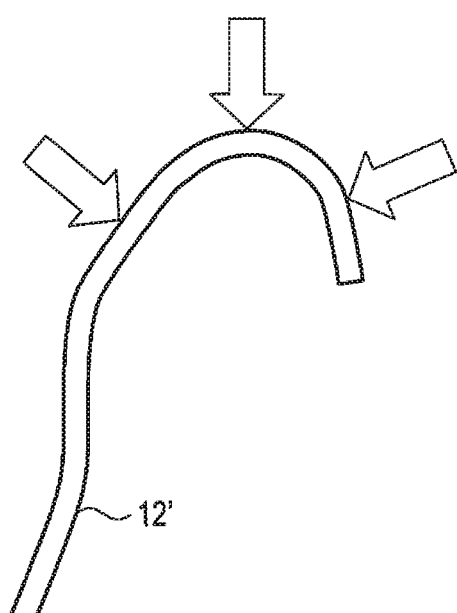
FIG. 15 is a view for explaining simplification of a position to which a force is applied.

For example, as illustrated in FIG. 15, three positions, that is, the apex of the bent portion and two points of a predetermined distance from the apex, are set as the positions to which force is applied.

In the case of the two-dimension, the parameters of the force are respectively the direction and the magnitude, and the total number is six.

In the case of the three-dimension, or in the case where the number of applied forces is larger, the number of parameters increases, but the parameters become clear and the calculations of Formula 4a to Formula 4d become possible.

As described above, the bending amount of each segment is obtained from the sensor 56, and the first bending moment Mb based on the bent shape is obtained from Formula 3 by the bending moment Mb calculation circuit 58A. In addition, based on the force information and Formula 4, the bending moment Mf calculation circuit 60A obtains the second bending moment Mf estimated from the force applied from the outside. At this time, the number of segments required to obtain the force variable must be equal to or larger than the number of variables. Usually, the number of segments is taken sufficiently larger and the optimization method is used to determine the value of the variable.

The number of simultaneous equations and variables when a plurality of forces are applied is as follows.

Simultaneous equations:

$$Mb_i = \Sigma Mf_{ji} \quad \text{(Formula 8)}$$

i=s~e i.e. ranging from s to e

Number of equations: $N_s$ (in the case of two-dimension) $3N_s$ (in the case of three-dimension)

Here, $Mf_{ji}$ is the bending moment applied to the segment $SG_i$ by the j-th applied force.

In addition, the variables to be obtained are as follows.

Variables at position j at which the force is applied: position, magnitude, and direction However, j=1 to $N_f$, and the position is the position in the longitudinal direction from the proximal or distal end.

Direction: direction around the longitudinal direction,

Number of variables at position j at which the force is applied: 2 (in the case of two-dimension (no direction)) $3N_f$ (in the case of three-dimension)

In the case where these simultaneous equations are applied to an example in which a plurality of forces are applied in two-dimension (within XY coordinates), similarly to the case where one force is applied, an example of an evaluation formula for applying the optimization method by using the position in the longitudinal direction as the position to which the force is applied and the direction with respect to the central axis (direction around the axis, that is, the angle with respect to the axis) as the direction 9504 of the force is shown in Formula 9 below.

$$\Sigma(\Sigma Mf_{ji} - Mb_i)^2 \quad \text{Evaluation formula}$$

i=s~e, i.e. ranging from s to e, $$j=1\sim N_f, \text{ i.e. ranging from 1 to } N_f \quad \text{(Formula 9)}$$

The optimization method is used to minimize the evaluation formula, and a desired variable of this formula is obtained.

When the assumed force is a load distribution, the number of variables to be obtained becomes extremely large and there is a possibility that no solution can be obtained. At this time, the load distribution may be processed by being replaced with a discrete distribution of force.

Figure 16A:
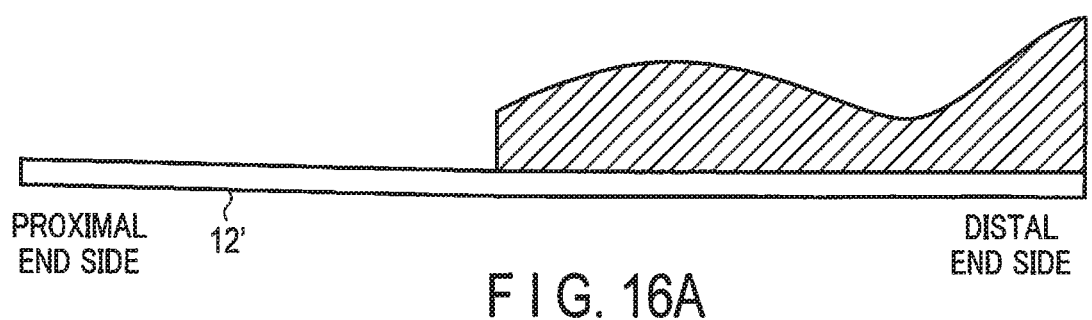
FIG. 16A is a view illustrating an assumed load distribution in which only the position and the magnitude of the force are displayed without regard to the directions of the bending and the force.
Figure 16B:
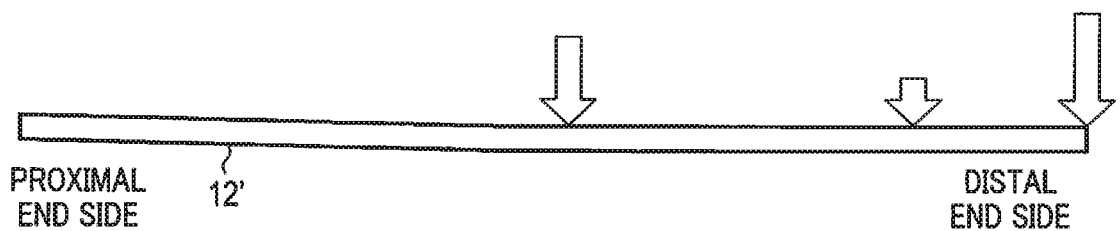
FIG. 16B is a view illustrating a simplified force arrangement in which only the position and the magnitude of the force are displayed without regard to the directions of the bending and the force.

FIGS. 16A and 16B illustrate the assumed load distribution and the simplified arrangement of the force, which are represented by only the position and magnitude of the force, neglecting the direction of the bending and the direction of force.

In practice, when applying the method of replacement with the distribution of discrete forces as illustrated in FIG. 16B, the number of variables may be narrowed by setting an upper limit on the number of forces. In addition, by appropriately narrowing the position, the direction, and the like to which the force is applied, the number of variables of a specific type can be increased and, for example, the number of positions can be increased.

In addition, if the result illustrated in FIG. 16B is obtained, the load distribution illustrated in FIG. 16A may be estimated based on the result and the estimated load distribution may be used as the force information.

[Segment Used for Calculation]

When the solution is obtained by the optimization method, the range of segments used for calculation reduces the processing amount of calculation and decreases the value of the evaluation formula per segment, that is, it is effective to improve the accuracy of the solution.

Figure 17A:
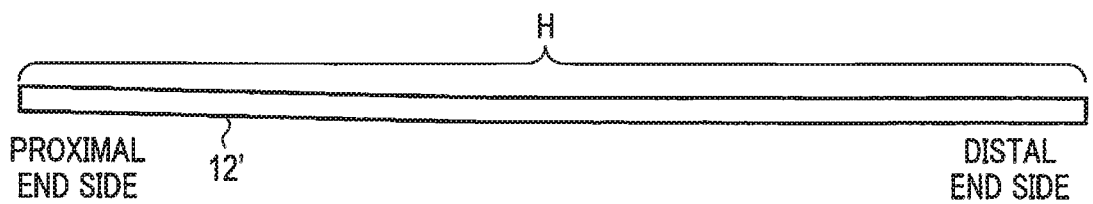
FIG. 17A is a view illustrating a full range (full segment) as an example of a range used for force detection.
Figure 17B:
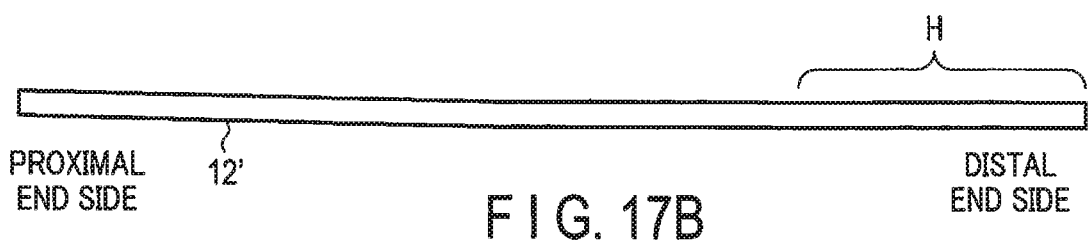
FIG. 17B is a view illustrating a predetermined range (segment) from the distal end as an example of a range used for force detection.
Figure 17C:
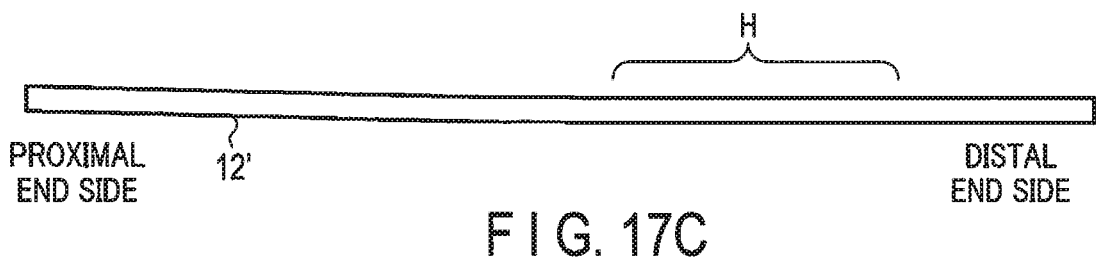
FIG. 17C is a view illustrating a predetermined range (segment) at the middle as an example of a range used for force detection.

An example of switching the segment that is the range of the endoscope insertion portion 12' used for calculating force information is illustrated by using FIG. 17A, FIG. 17B, and FIG. 17C. These drawings illustrate only the range, ignoring the bending of the endoscope insertion portion 12'.

Figure 18A:
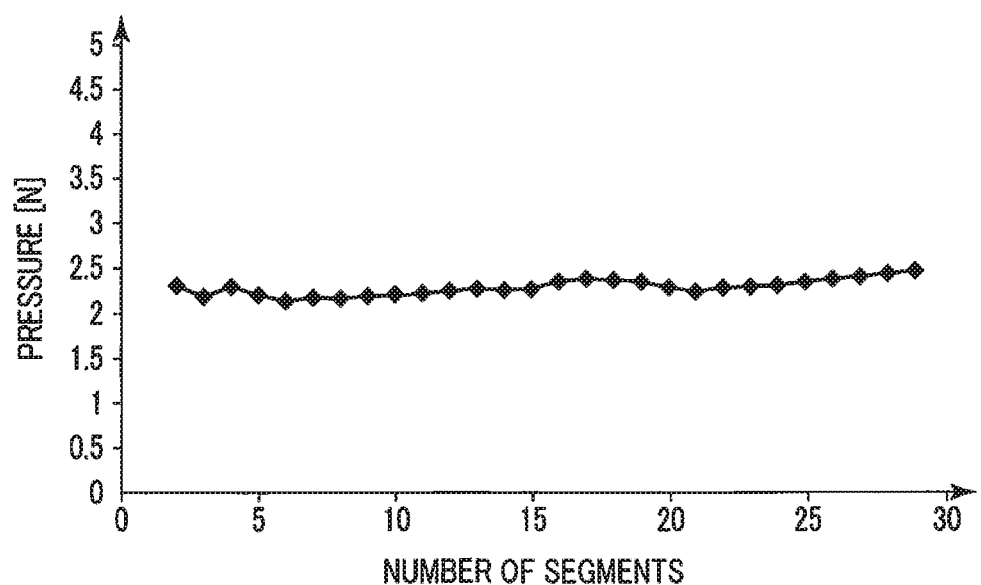
FIG. 18A is a view illustrating an example of a relationship between a force and the number of segments.

FIG. 17A is an example of calculating force information by using all segments as the range H used for calculating force information. In this case, the detection accuracy of the force information can be enhanced by establishment of Formula 6 or 8 in all the segments. For example, a case where the relationship between the magnitude of the force and the segment used for calculation is in the relationship illustrated in FIG. 18A is this example.

In addition, when the number of variables to be obtained is large, it is necessary to use more segments, and if this is followed, all segments will be used.

FIG. 17B is an example of calculating force information by using a segment in a predetermined range from the distal end as the range H used for calculating force information. This is at least a case where Formula 6 is established in the segment on the distal end side and the number of segments required to obtain the value of the variable is not so much (the case of FIG. 18A or the like).

Figure 18B:
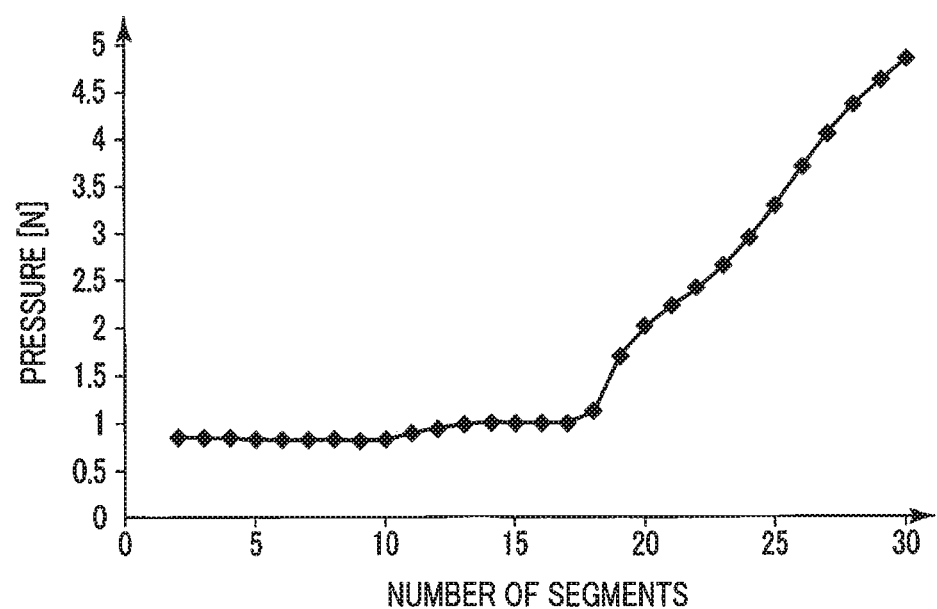
FIG. 18B is a view illustrating another example of a relationship between a force and the number of segments.

In addition, a case where only the force applied to the distal end is obtained, but when the force is also applied to the middle portion and it is desired to remove this effect, the value of the variable is obtained in the segment before the position of the force acting on the middle portion is such an example. At this time, when the number of segments is increased, the value of Formula 7 that is the evaluation formula per segment is as illustrated in FIG. 18B. At this time, the range H used for calculating the force information should be set before the value of the evaluation formula per segment changes significantly. As described above, the range H used for calculating the force information based on the value of the evaluation formula per segment is not obtained, and the accuracy of the force information can be further improved by calculating the force information based on the calculated force information, particularly the magnitude of the force, instead of the value of the evaluation formula per segment.

FIG. 17C is an example of calculating force information by using a segment in a predetermined range in the middle as the range H used for calculating force information. This is at least a case where Formula 6 is established in the segment in the middle and the number of segments required to obtain the value of the variable is not so much (the case of FIG. 18A or the like).

In addition, a case where only the force applied to a slightly more proximal side than the distal end portion is obtained, but when the force is also applied to the middle portion of a more proximal side and it is desired to remove this effect, the value of the variable is obtained in the segment before the position of the force acting on the middle portion is such an example.

In particular, when the shape in a state in which no force is applied to the bent portion 32 on the distal end side is unknown, it is preferable to perform the processing of Formula 6 by excluding that portion. In such a case, when the number of segments is increased, the value of Formula 7 that is the evaluation formula per segment is as illustrated in FIG. 18B. At this time, the range H used for calculating the force information should be set before the value of the evaluation formula per segment changes significantly. As described above, the range H used for calculating the force information based on the value of the evaluation formula per segment is not obtained, and the accuracy of the force information can be further improved by calculating the force information based on the calculated force information, particularly the magnitude of the force, instead of the value of the evaluation formula per segment.

From the above, based on the description of FIGS. 17B and 17C, when a force is applied to a plurality of points of the endoscope insertion portion 12', the number of variables to be obtained at a time can be reduced by sequentially performing detection from the force applied close to the distal end of the endoscope insertion portion 12'. This can improve the efficiency of the calculation processing and obtain the applied force with a smaller number of segments than obtaining the variables for all applied forces at once.

As a specific example, a case where the position to which the force is applied is position P1 to position P3 will be described.

When variables relating to position P1 to position P3 are obtained simultaneously and collectively, it is necessary to obtain three times the variables per position. On the other hand, when position P1, position P2, and position P3 are obtained in this order, the number of variables to be obtained per one time becomes equal to the variables per position. In addition, if it is difficult to process three at the same time but two can be processed, position P1 and position P2 may be processed simultaneously in the order of (P1 and P2) and P3, and position P2 and position P3 may be processed simultaneously in the order of position P1 and (position P2 and position P3).

That is, in Formulae 8 and 9, in order to reduce the variables to be obtained simultaneously, the range of the segment $SG_i$ that calculates the bending moment is limited, the values of the variables are sequentially obtained, the obtained variables are regarded as constants thereafter, and the remaining variables are obtained, thereby reducing the burden of optimization processing.

At this time, the range of the segment $SG_i$ is, for example, until the first force is applied from the distal end side, or until the second force is applied. In this manner, in order to perform optimization, the range of the segment $SG_i$ shifts one by one.

[Object Influence Determination Circuit 50]

The object influence determination circuit 50 determines the influence of the force information calculated by the force calculation circuit 48 or 48 A on the object O based on the determination criteria stored in the determination criteria memory circuit 62. Here, the determination criteria memory circuit 62 may store a plurality of stepwise determination criteria, and may determine the influence of a plurality of stages. The determination criteria memory circuit 62 may store one determination criteria, and may make a binary determination as to whether there is an influence.

In addition, there are a plurality of types in the influence of the force information on the object O, at least one type of determination criteria is stored in the determination criteria memory circuit 62, and the object influence determination circuit 50 may determine the influence of the force information on the object O based on the determination criteria.

For example, as illustrated in FIG. 19A, the object influence determination circuit 50 can include a determination criteria memory circuit 62 and an influence-on-object determination circuit 104. Here, the determination criteria memory circuit 62 stores, as the determination criteria, the degree of damage given to the object O, such as pain, breakage, or perforation given to the object O as the influence of the force information on the object O. The influence-on-object determination circuit 104 determines the degree of damage given to the object O based on the determination criteria, and outputs the result as the influence determination result.

Alternatively, as illustrated in FIG. 19B, the object influence determination circuit 50 can include a determination criteria memory circuit 62 and an influence-on-object-function determination circuit 106. Here, the determination criteria memory circuit 62 stores, as the determination criteria, the degree of damage given to the function of at least part of the object O as the influence of the force information on the object O. The influence-on-object-function determination circuit 106 determines degree of the influence on the function of at least part of the object O based on the determination criteria, and outputs the result as the influence determination result.

In addition, as illustrated in FIG. 19C, the object influence determination circuit 50 can include a determination criteria memory circuit 62 and an object (part) deformation and movement determination circuit 108. Here, the determination criteria memory circuit 62 stores, as the determination criteria, the degree of deformation and the degree of movement in the part of the object O to which the force is applied and/or its periphery as the influence of the force information on the object O. The object (part) deformation and movement determination circuit 108 determines the degree of deformation and movement in the part of the object O to which the force is applied and/or its periphery based on the determination criteria, and outputs the result as the influence determination result.

The object influence determination circuit 50 may include two or more of an influence-on-object determination circuit 104, a determination criteria memory circuits 62 and influence-on-object-function determination circuit 106, and an object (part) deformation and movement determination circuit 108. Furthermore, the object influence determination circuit 50 may further include a circuit that determines the influence of force information other than these on the object O. Instead of these, the object influence determination circuit can include a circuit that determines the influence of other force information on the object O.

[Information Presentation Device or Driving Feedback Circuit 52]

The information presentation device or driving feedback circuit 52 provides an operator or driving circuit 110 with at least one of the force information obtained from the force calculation circuit 48 or 48A and the influence determination result obtained from the object influence determination circuit 50, or information processed to be directed to the transmission contents as appropriate based on the information. The information presentation device in the information presentation device or driving feedback circuit 52 provides information to an operator in the operator or driving circuit 110. The driving feedback circuit in the information presentation device or driving feedback circuit 52 provides information to the driving circuit in the operator or driving circuit 110.

That is, the information presentation device processes at least one of the force information obtained from the force calculation circuit 48 or 48A and the influence determination result obtained from the object influence determination circuit 50, or presentation information to be presented to the operator as appropriate based on the information, and provides the presentation information to the operator. Specifically, as the information presentation device, a monitor screen, an audio device, a vibrating device or an electrical stimulation device provided in the operation portion 28 of the endoscope 16, and the like can be considered. In addition, as the method of presenting the information by the information presentation device, characters, symbols, figures, images, and the like can be considered, when taking the monitor screen as an example. The configuration and method of these information presentation may use a plurality of configurations and methods at the same time, or may be switched and used according to the degree of the force information or the influence determination result.

In addition, the driving feedback circuit is the configuration assuming that part of the driving system of the endoscope insertion portion 12' is motorized or automated as the driving circuit. For example, the case where insertion and removal of the endoscope insertion portion 12' are performed by the insertion manipulator is assumed. The driving feedback device processes at least one of the force information obtained from the force calculation circuit 48 or 48A and the influence determination result obtained from the object influence determination circuit 50, or driving information for feedback to the driving circuit as appropriate based on the information, and provides the presentation information to the driving circuit.

[Memory Circuit 54]

The memory circuit 54 stores at least one of the presentation information or driving information fed back to the operator or driving circuit 110 by the information presentation device or driving feedback circuit 52. In addition, the memory circuit 54 can store the coordinates and deformation information measured by the coordinate and deformation state measurement circuit 44, or the coordinates and shape measured by the coordinate and shape measurement circuit 44A. As described above, by storing the presentation information or the driving information together with the coordinate and deformation information or the shape, it is possible to confirm later the generation position of the force, the shape of the portion at the time of the generation of the force, and the like.

[Large Intestine Endoscope]

In a case where the object O and the insertion target are a human and a body cavity, in particular, the large intestine is a body cavity having a complicated shape, individual differences, and a portion that is not determined or fixed. Among the body cavities, the positions of the large intestine, such as a sigmoid colon or a transverse colon, are easily changed. Therefore, the degree of difficulty in inserting the endoscope 16 or the like into the large intestine is high. For example, the intestine may be stretched at the side of the endoscope insertion portion 12', or the distal end of the endoscope insertion portion 12' bites into the intestine, thereby putting a heavy load on the intestine or stagnating insertion on the way.

At that time, the force applied to the endoscope insertion portion 12' when the operator or the insertion manipulator inserts and removes the endoscope insertion portion 12' is the standard of the load in the intestine. In addition, quantifying the relationship between the force amount of insertion and the force applied to the endoscope insertion portion 12' in the body cavity is important reference information for grasping the situation at the time of the insertion operation.

Figure 20A:
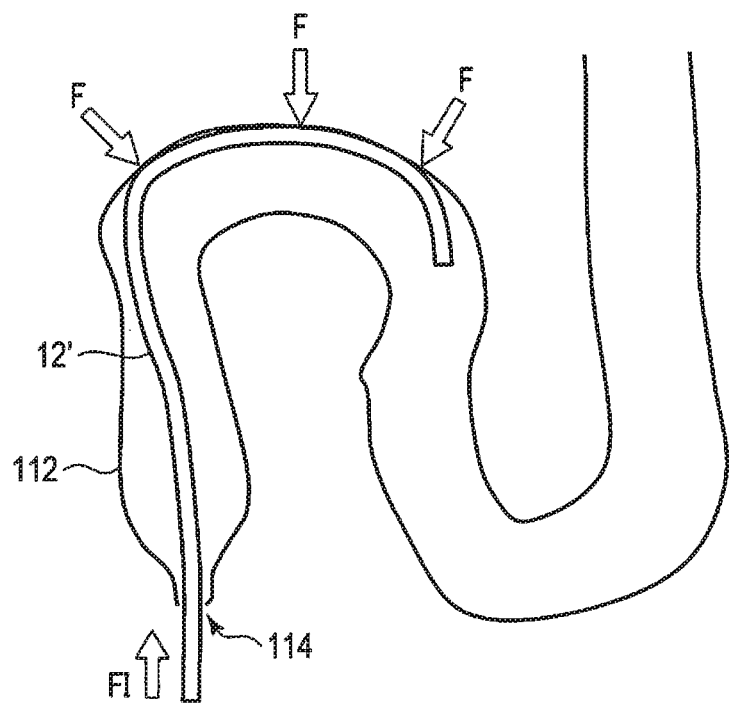
FIG. 20A is a view illustrating a state in which an endoscope insertion portion is inserted from an anus to a sigmoid colon.

For example, FIG. 20A illustrates a state in which the endoscope insertion portion 12' of the large intestine endoscope targeting the large intestine 112 is inserted from the anus 114 to the sigmoid colon.

The force applied to the endoscope insertion portion 12' of the large intestine endoscope includes a force F applied to the inside of the large intestine 112, a force applied from the vicinity of the anus 114, an insertion and removal force FI received from the operator or the insertion manipulator, and the like. Here, the inside of the large intestine 112 does not include the vicinity of the anus 114.

From the balance of the forces, it is estimated that the resultant force of the forces applied to the endoscope insertion portions 12' of the large intestine endoscope is approximately zero.

Among the forces applied to the endoscope insertion portion 12' of the large intestine endoscope, the main force is the insertion and removal force FI received from the operator or the insertion manipulator and the (resultant force of) the force F applied to the inside of the large intestine 112. If these are balanced, that is, when the resultant force becomes zero, it is possible to determine the insertion and removal force FI received from the operator or the insertion manipulator.

Due to this method, it is possible to obtain the magnitude of the insertion and removal force FI, which is the force applied by the operator or the insertion manipulator for the insertion and removal of the endoscope insertion portion 12' of the large intestine endoscope.

When the force received in the vicinity of the anus 114 is also obtained by estimation similarly to the force F applied to the inside, the resultant force of the force F applied to the inside of the large intestine 112 and the force received from the vicinity of the anus 114 may be balanced with the insertion and removal force FI applied in order for the operator or the insertion manipulator to insert/remove the endoscope insertion portion 12' of the large intestine endoscope. In addition, when the force received from the vicinity of the anus 114 is not obtained by estimation, friction due to tightening is the main, and thus this force may be ignored.

As described above, the insertion and removal force FI can be obtained from only the coordinates, deformation information, or shape information of the endoscope insertion portion 12' of the large intestine endoscope.

Even if roughly calculated, since a rough insertion and removal force FI can be obtained, the operation of the operator or the insertion manipulator can be grasped simply and quantitatively, which can lead to the prevention of applying an excessive force.

The flexible tubular portion 12 is not limited to the endoscope insertion portion 12' of the large intestine endoscope, and may be an endoscope insertion portion 12' of another endoscope, a medical manipulator, a catheter, or the like.

Figure 20B:
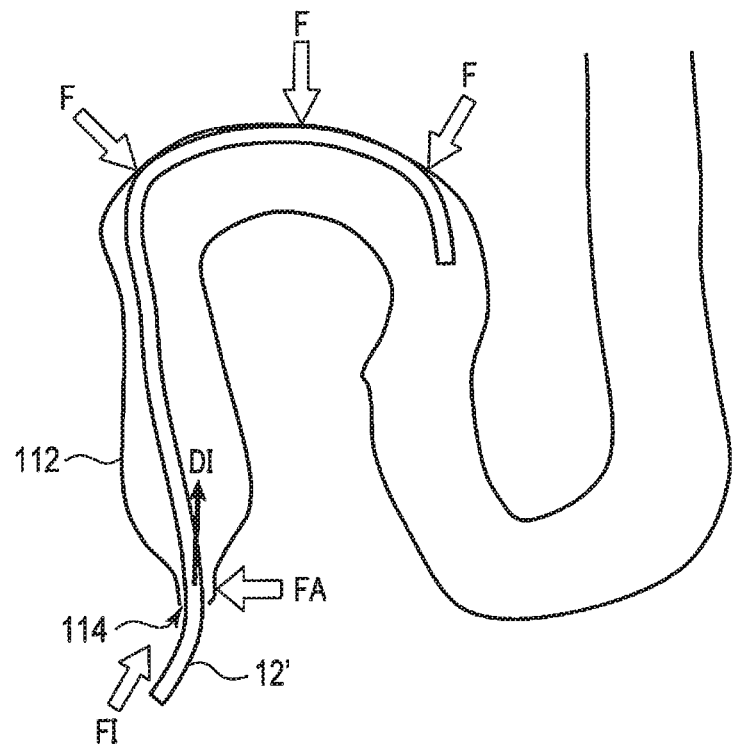
FIG. 20B is a view illustrating another example of a state in which an endoscope insertion portion is inserted from an anus to a sigmoid colon.

In addition, FIG. 20B illustrates another example of a state in which the endoscope insertion portion 12' of the large intestine endoscope is inserted up to the sigmoid colon. In this example, when inserting the endoscope insertion portion 12', the endoscope insertion portion 12' is inserted obliquely to the vicinity of the anus 114.

In the example in which the endoscope insertion portion 12' is obliquely inserted into the anus 114, a force for tightening the endoscope insertion portion 12' and a force for bending the endoscope insertion portion 12' obliquely entered act as the force applied to the endoscope insertion portion 12' in the vicinity of the anus 114. The resultant force of the forces applied to the endoscope insertion portion 12' in the vicinity of the anus 114 becomes the force applied from the side as the force FA applied to the anus.

In this case as well, the forces applied to the endoscope insertion portion 12' of the large intestine endoscope are substantially balanced, that is, the resultant force is substantially zero. In particular, considering the components of these applied forces in the insertion direction (indicated by an arrow DI in the drawing) in the vicinity of the anus 114, the sum of these components is approximately zero. If the friction in the vicinity of the anus 114 is neglected, the force applied in the vicinity of the anus 114 can be excluded from the calculation by considering the insertion direction component in the vicinity of the anus 114. That is, it is sufficient to calculate only the force F applied to the inside of the large intestine 112 and the insertion and removal force FI, excluding the anus 114.

As described above, it is possible to obtain the insertion direction component in the vicinity of the anus 114 in the amount of the insertion and removal force FI of the endoscope insertion portion 12'.

As the approximation, the insertion direction component in the vicinity of the anus 114 may be regarded as the force amount of the insertion and removal force FI. In addition, if an angle between the insertion and removal direction and the insertion direction in the vicinity of the anus 114 is known, an approximate value of the force amount of the insertion and removal force FI is obtained through division by the cosine of that angle.

As described above, it is possible to obtain the insertion and removal force FI of the endoscope insertion portion 12', and make a determination based on the force amount of the force FI.

[Software Configuration]

All or part of the components of the force estimation systems 14 and 14A excluding the sensor 56 as described above may not be configured as a hardware circuit. That is, the computer processor (not illustrated) and the memory provided in the housing 102 are accommodated, a software program for causing the computer processor to function as all or part of the components is prepared in the memory, and a processor executes that program. In this manner, the processor may be configured to perform at least one of the functions of the components. Alternatively, the software program as described above is stored in a memory (not illustrated) provided in the control device 26, and a processor (not illustrated) of the control device 26 executes the program. In this manner, the processor of the control device 26 may be configured to perform at least one of the functions of the components described above. Furthermore, if the desired result is obtained, a processor and a memory of a server device which can be provided at a remote place from the endoscope system 10' and can be accessed by the control device 26 by wired or wireless communication may be used.

Figure 21:
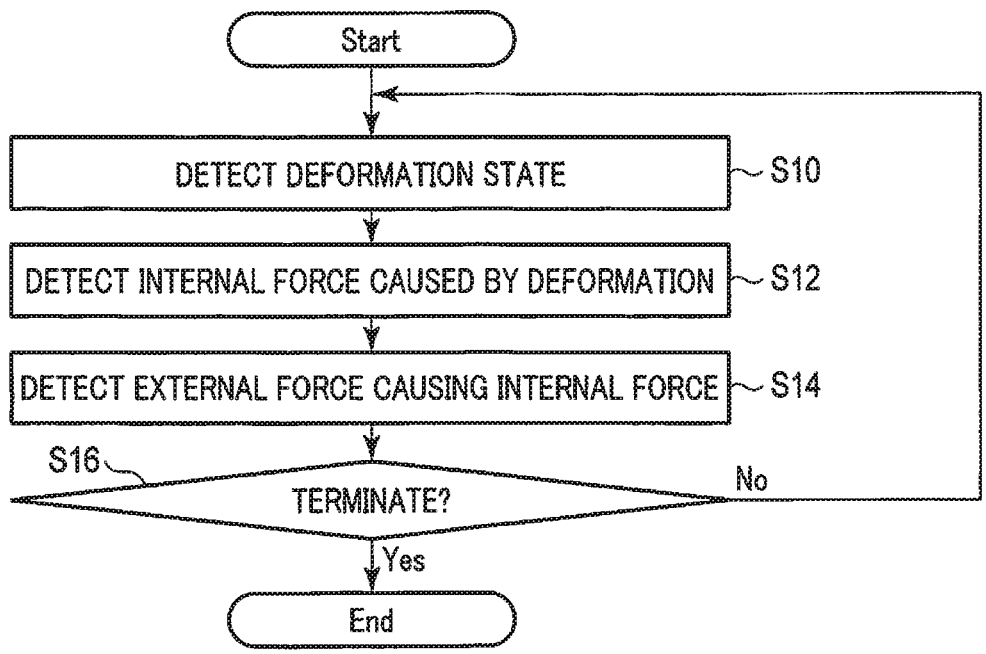
FIG. 21 is a view illustrating a flowchart for explaining a force information calculation method for obtaining an external force based on a general internal force.

For example, in the case where the coordinate and deformation state measurement circuit 44 excluding the sensor 56 and the force calculation circuit 48 are configured by software, a software program for performing an operation as illustrated in FIG. 21 is stored in a memory (not illustrated), and when a processor (not illustrated) executes the program, the processor can function as the coordinate and deformation state measurement circuit 44 excluding the sensor 56 and the force calculation circuit 48.

That is, the processor detects the deformation of the endoscope insertion portion 12' in a specific range from the detection result of the sensor 56 (step S10). Thereafter, the processor detects the internal force caused by the deformation of the endoscope insertion portion 12' based on the detected deformation and the mechanical characteristic information stored in the mechanical characteristic memory circuit 46 (step S12). Then, based on the detected internal force, the processor detects the external force causing the internal force, that is, the force information (step S14). The processor repeats the processes of steps S10 to S14 until a predetermined termination instruction is given from the operator or the like (step S16).

Therefore, the processor can efficiently detect the external force causing the deformation by detecting only the deformation of the endoscope insertion portion 12', without directly measuring the force.

Figure 22:
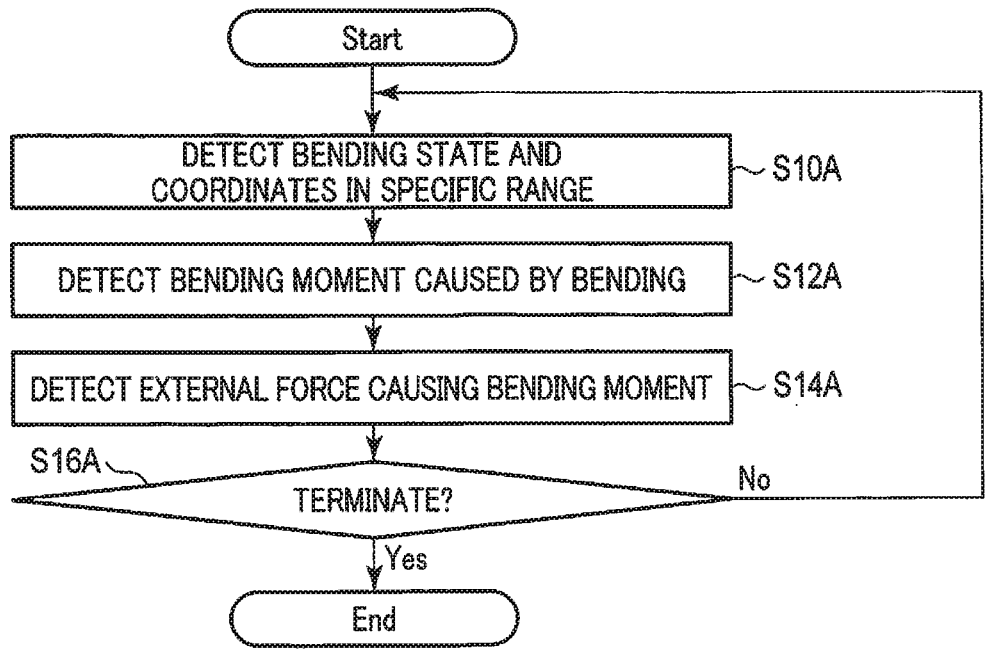
FIG. 22 is a view illustrating a flowchart for explaining a force information calculation method for obtaining an external force based on a bending moment that is one of internal forces.

In addition, in the case where the coordinate and shape measurement circuit 44A excluding the sensor 56 and the force calculation circuit 48A are configured by software, a software program for performing an operation as illustrated in FIG. 22 is stored in a memory (not illustrated), and when a processor (not illustrated) executes the program, the processor can function as the coordinate and shape measurement circuit 44A excluding the sensor 56 and the force calculation circuit 48A.

That is, the processor detects the bending state (shape) and coordinates of the endoscope insertion portion 12' in a specific range from the detection result of the sensor 56 (step S10A). Thereafter, the processor detects the bending moment caused by the bending of the endoscope insertion portion 12' based on the detected bended state information and the bending stiffness information stored in the bending stiffness memory circuit 46A (step S12A). Then, based on the detected bending moment, the processor detects the external force causing the bending moment, that is, the force information (step S14A). The processor repeats the processes of steps S10A to S14A until a predetermined termination instruction is given from the operator or the like (step S16A).

Therefore, the processor can efficiently detect the external force causing the bending by detecting only the bending state and the coordinates of the endoscope insertion portion 12', without directly measuring the force.

Figure 23:
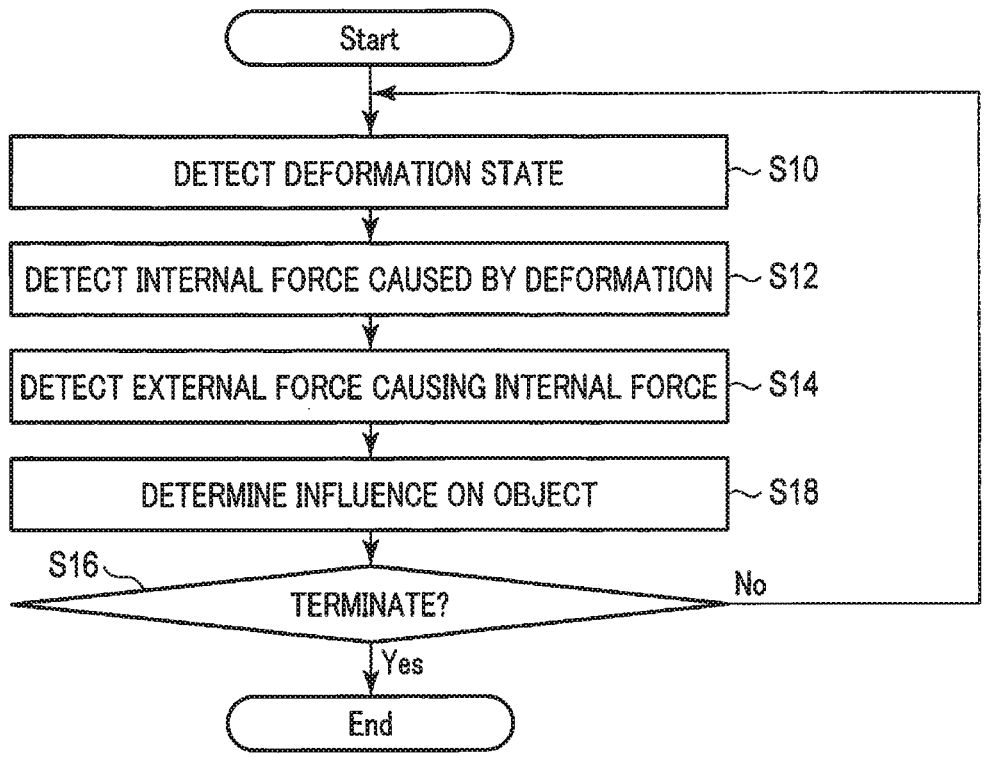
FIG. 23 is a view illustrating a flowchart for explaining a modification of the force information calculation method of FIG. 21.

In addition, in the case where the coordinate and deformation state measurement circuit 44 excluding the sensor 56, the force calculation circuit 48, and the object influence determination circuit 50 are configured by software, a software program for performing an operation as illustrated in FIG. 23 is stored in a memory (not illustrated), and when a processor (not illustrated) executes the program, the processor can function as the coordinate and deformation state measurement circuit 44 excluding the sensor 56, the force calculation circuit 48, and the object influence determination circuit 50.

That is, the processor detects the external force causing the internal force, that is, the force information by the processes of steps S10 to S14 described above with reference to FIG. 21, and then determines the influence on the object O, which is caused by the external force (step S18). Then, the processor repeats the processes of steps S10, S12, S14, and S18 until a predetermined termination instruction is given from the operator or the like (step S16).

Therefore, the processor can efficiently detect the external force causing the deformation by detecting only the deformation of the endoscope insertion portion 12', without directly measuring the force, and can further efficiently and quantitatively determine the influence on the object O based on the detected external force.

Figure 24:
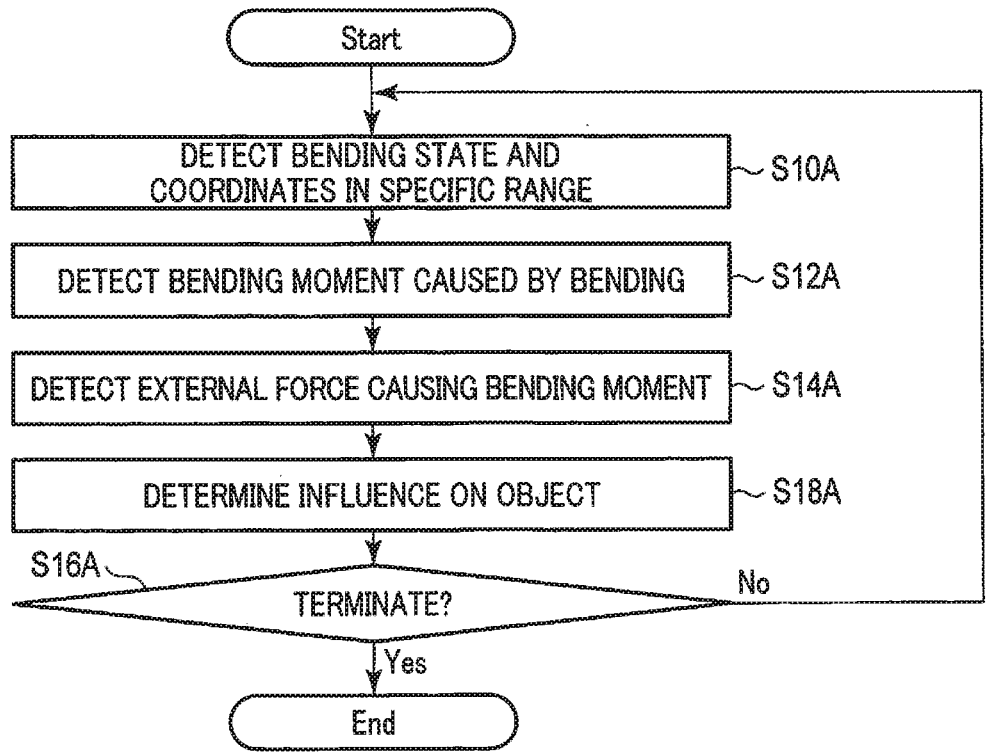
FIG. 24 is a view illustrating a flowchart for explaining a modification of the force information calculation method of FIG. 22.

In addition, in the case where the coordinate and shape measurement circuit 44A excluding the sensor 56, the force calculation circuit 48A, and the object influence determination circuit 50 are configured by software, a software program for performing an operation as illustrated in FIG. 24 is stored in a memory (not illustrated), and when a processor (not illustrated) executes the program, the processor can function as the coordinate and shape measurement circuit 44A excluding the sensor 56, the force calculation circuit 48A, and the object influence determination circuit 50.

That is, the processor detects the external force causing the bending moment, that is, the force information by the processes of steps S10A to S14A described above with reference to FIG. 22, and then determines the influence on the object O, which is caused by the external force (step S18A). Then, the processor repeats the processes of steps S10A, S12A, S14A, and S18A until a predetermined termination instruction is given from the operator or the like (step S16A).

Therefore, the processor can efficiently detect the external force causing the bending by detecting only the bending state and coordinates of the endoscope insertion portion 12', without directly measuring the force, and can further efficiently and quantitatively determine the influence on the object O based on the detected external force.

As described above, the force estimation system 10 according to the first embodiment of the present invention includes a force estimation system 14 as a force information calculation unit, which calculates force information about the forces applied to one or more positions of the flexible tubular portion 12 (position, direction, and/or magnitude of force) through an arithmetic operation, based on the deformation state (for example, shape) and mechanical characteristics (from no load state) at a plurality of longitudinal positions of the flexible tubular portion 12 having flexibility.

Therefore, the force information can be easily calculated only in the deformation state even without directly measuring the force. Therefore, since a force sensor is unnecessary, space saving can be achieved, and the diameter reduction of the flexible tubular portion 12 having flexibility can be achieved.

Here, the force estimation system 14 calculates the force information about the forces applied to the one or more positions of the flexible tubular portion 12 through an arithmetic operation, based on the (almost) balance between the first internal force (that is, force or moment) estimated from the deformation state and the mechanical characteristic and generated at the plurality of longitudinal positions of the flexible tubular portion 12 and the periphery thereof and the second internal force generated at the plurality of longitudinal positions of the flexible tubular portion 12 and the periphery thereof by the force (that is, external force) applied to the one or more positions of the flexible tubular portion 12.

Therefore, the force information can be estimated from the balance of static forces.

That is, since the force information can be calculated from static analysis, there is no need to solve the motion equation for each segment, and the speed can be increased and real-time processing is easy. Therefore, force information at more positions is obtained.

In addition, the force information can be easily calculated only in the shape (deformation state) even without directly measuring the force. Therefore, since a force sensor is unnecessary, space saving can be achieved, and the diameter reduction of the flexible tubular portion 12 can be achieved.

In this case, the deformation state is a bending state, the mechanical characteristic is bending stiffness, and the force estimation system 14 calculates the force information about the forces applied to the one or more positions of the flexible tubular portion 12 through an arithmetic operation, based on the (almost) balance between the first bending moment estimated from the deformation state and the mechanical characteristic and generated at the plurality of longitudinal positions of the flexible tubular portion 12 and the periphery thereof and the second bending moment generated at the plurality of longitudinal positions of the flexible tubular portion 12 and the periphery thereof by the force applied to the one or more positions of the flexible tubular portion 12.

As described above, highly accurate detection can be performed by estimating the force information from the balance of the forces related to the bending, which is particularly sensitive even in the deformation state.

In addition, the force estimation system 14 may include a coordinate and shape measurement circuit 44A serving as a coordinate and shape measurement unit that measures or estimates coordinates and shape (information) (curvature, bending amount, bending angle, or the like) at a plurality of longitudinal positions of the flexible tubular portion 12, a bending stiffness memory circuit 46A serving as a mechanical property memory unit that stores bending stiffness at the plurality of positions, and a force calculation circuit 48A serving as a force calculation unit that calculates the force information about the forces applied to the one or more positions of the flexible tubular portion 12 through an arithmetic operation.

The force calculation circuit 48A can calculate (estimate) the internal forces at the plurality of positions from the information of the coordinate and shape measurement circuit 44A arranged in the system and the information of the bending stiffness at the plurality of positions. Furthermore, it is possible to calculate (estimate) the force information that causes the internal forces at the plurality of positions.

In this manner, since the components in the system includes the force calculation circuit 48A that performs calculation necessary for balancing the forces, that is, calculates such external force, force information at one or more positions are obtained from coordinates and shape change and bending stiffness from a state in which no force is applied at a plurality of positions.

In addition, since the force information is calculated from the static balance, there is no need to solve the motion equation for each segment. Therefore, the speed can be increased, real-time processing becomes easy, and force information at more positions is obtained.

In addition, the force information can be easily calculated only by the coordinates and the shape, without directly measuring the force. Therefore, the force sensor is not required, space can be saved, and the diameter of the flexible tubular portion 12 can be reduced.

In this case, the coordinate and shape measurement circuit 44A includes at least one of a position sensor 64 and a shape sensor 66, which are incorporated in the flexible tubular portion 12 or a portion adjacent to the flexible tubular portion 12, or are detachably attached to the flexible tubular portion 12 or a portion adjacent to the flexible tubular portion 12, and can measure the coordinates and the shape of a portion including at least part of the flexible tubular portion 12. The coordinate and shape measurement circuit 44A can measure the coordinates and the shape at the plurality of positions based on the output of at least one of the position sensor 64 and the shape sensor 66.

Therefore, since it does not depend on external information such as image information, the force information can always be calculated regardless of the arrangement relationship of the operator, the object O, and the sensor.

Here, the coordinate and shape measurement circuit 44A measures the coordinates and the shape at the plurality of positions by not only processing the value of the output of at least one of the position sensor 64 and the shape sensor 66 but also performing estimation (by interpolation processing or the like).

That is, finer segment setting can be performed by estimation using interpolation processing or the like, and the force information, such as the position, direction, and magnitude, to which force is applied can be detected with high accuracy. Therefore, even if the number of position sensors 64 or the number of shape sensors 66 is small, it is possible to calculate the position and the shape closer to the actual ones.

In addition, the force calculation circuit 48A includes a bending moment Mb calculation circuit 58A serving as a first bending moment calculation unit that calculates curvature at each position from information about the shapes at the plurality of positions and calculates a first bending moment Mb at the plurality of positions, which is calculated from the curvature and the bending stiffness, and a bending moment Mf calculation circuit 60A serving as a second bending moment calculation unit that calculates a second bending moment Mf at the plurality of positions, which is calculated from the forces applied to the one or more positions of the flexible tubular portion 12. The force information applied to the one or more positions of the flexible tubular portion 12 may be calculated based on the fact that the second bending moment Mf and the first bending moment Mb substantially coincide with each other at the plurality of positions.

By utilizing the specific formula of the static balance and the parameters used for the formula in this way, how to perform the numerical calculation becomes clear and the numerical calculation can be performed.

Since the force information can be obtained by such a simple mathematical expression, calculation is easy and high speed processing is possible. Therefore, real-time calculation of force information and calculation of force information at many positions are possible.

in this case, the number of formulae derived from the balance between the first bending moment and the second bending moment at the plurality of positions is larger than the number of variables of the force information calculated by the force calculation circuit 48A, and the force calculation circuit 48A calculates the force information by using the optimization method for minimizing the evaluation formula (error or the like).

That is, when the number of simultaneous equations is larger than the number of variables (parameters) to be obtained, the force information as a variable can be determined by using the optimization method for minimizing the evaluation formula.

In particular, the force information that minimizes the error can be obtained by using the evaluation formula as the error.

When the evaluation formula is a simple polynomial, it is possible to solve the evaluation formula, in particular, by the least square method.

Such an optimization method is high in both calculation speed and accuracy.

Here, the one or more positions of the flexible tubular portion 12 are plural, and the force calculation circuit 48A calculates the force information in the order from the position on the distal end side of the flexible tubular portion 12 among the plurality of positions of the flexible tubular portion 12.

As described above, when calculating the force information at one or more positions, it is possible to reduce the calculation amount and increase the calculation speed by calculating the force information at one position as much as possible.

Alternatively, the plurality of positions used for the second bending moment Mf and the first bending moment Mb may be limited based on the evaluation formula or the calculated force information (the magnitude or the like of the force).

That is, in order to obtain the force information, it is not necessary to perform calculation using information, such as coordinates, shapes, and bending stiffness, at the plurality of positions.

In addition, when the force is applied at an unexpected position, and when the calculation is performed by using the information at that position, the value of the evaluation formula increases, and information different from the force information that is actually added may be obtained.

Therefore, by calculating the force information based on the value of the evaluation formula or the calculated force information, particularly the magnitude of the force, the accuracy of the force information can be further improved.

In addition, the force calculation circuit 48A preferably calculate the force information by applying the force actually applied to the flexible tubular portion 12 to a simplified model.

That is, in a case where the force is applied at many positions, or in a case where the force is applied like the load distribution, if the force information is intended to be correctly obtained, the number of pieces of the force information (variables) to be obtained become huge. Furthermore, when the number of pieces of force information to be obtained becomes larger than the number of static balance formulae, the force information can be obtained.

As the number of pieces of force information to be obtained is larger, more static balance formulae are required, and it takes a longer time to process. Therefore, calculation becomes possible and processing time can be reduced by simplifying the force information to be obtained and reducing the number of variables.

Simplification is possible by applying the force actually applied to the flexible tubular portion 12 to the simplified model and performing calculation. If simplified, it is also possible to obtain other items in more detail.

In this case, when the force applied to the flexible tubular portion 12 is the load distribution force, the force calculation circuit 48A can apply the load distribution force to the simplified model of the force applied to a finite point of the flexible tubular portion 12, and can perform the calculation of the force information.

In particular, in the body cavity, the contact with the endoscope insertion portion 12' of the endoscope or the like occurs at the surface rather than at the point. In consideration of all the contact portions, the positions of the applied force become innumerable. By reducing the number of positions to which the force is applied, so that one point or less is set to one segment within the contact range, the number of variables to be obtained can be reduced, processing time can be reduced, processing is possible, and other items can be obtained in detail.

Alternatively, there are a plurality of forces applied to the flexible tubular portion 12, and the force calculation circuit 48A may calculate the force information by apply to the simplified model in which the flexible tubular portion 12 and the position and the direction in which the actually applied force acts are on one plane.

In this manner, by limiting the direction of the force in one plane, the number of variables to be obtained can be reduced, processing time can be reduced, processing is possible, and other items can be obtained in detail.

In particular, by setting the one plane to a plane substantially perpendicular to gravity, it is possible to exclude the influence of gravity.

Further, the force calculation circuit 48A may perform the calculation of the force information by applying to the simplified model in which the direction of the force applied to the flexible tubular portion 12 is substantially perpendicular to the flexible tubular portion 12.

That the direction of the force applied to the flexible tubular portion 12 is substantially perpendicular to the flexible tubular portion 12 means that the friction force is not almost generated. In particular, when inserting the endoscope insertion portion 12' of the endoscope or the like into the body cavity, a lubricant is sufficiently used to reduce the resistance between the body cavity and the endoscope. Therefore, the friction force acting on the side surface of the endoscope insertion portion 12' is often small, and as a result, the direction of the force applied to the endoscope insertion portion 12' is often substantially vertical. In this manner, by reducing the variable of the direction in which the force is applied, the number of variables to be obtained can be reduced, processing time can be reduced, processing is possible, and other items can be obtained in detail.

Alternatively, the force calculation circuit 48A estimates the force actually applied to the flexible tubular portion 12 based on the force information calculated by applying to the simplified model.

When the final answer is shown as the load distribution, it is possible to find how to add the force close to the actual state by changing the simplified answer to the distribution state answer.

When making the distribution state, the distribution state may be obtained by approximation without necessarily considering that the balance formula is established and the value of the evaluation formula does not change depending on the accuracy of the target. Conversely, the distribution state may be obtained more strictly by establishing the balance formula or keeping the value of the evaluation formula unchanged.

In this case, the force calculation circuit 48A calculates the force information by applying the force applied to the flexible tubular portion 12 in the load distribution to the model simplified to the force applied to the finite point on the flexible tubular portion 12, and estimates the force actually applied to the flexible tubular portion 12 on the assumption that it is a load distribution, from the force information calculated by estimating that it is applied to the finite point.

That is, when the final answer is shown as the load distribution, it is possible to find how to add the force close to the actual state by changing the simplified answer to the distribution state answer.

When making the distribution state, the distribution state may be obtained by approximation without necessarily considering that the balance formula is established and the value of the evaluation formula does not change depending on the accuracy of the target. Conversely, the distribution state may be obtained more strictly by establishing the balance formula or keeping the value of the evaluation formula unchanged.

In addition, the flexible tubular portion 12 can further include an object influence determination circuit 50 serving as an object influence determination unit, which is inserted into the object O and determines the influence of the force information calculated by the force calculation circuit 48A on the object O.

In this manner, not only by simply obtaining the force information but also by determining the influence on the object O, information such as stability, presence or absence of problems, or the like regarding the operation of the operator or the operation of the system can be generated, and it is possible to consider concrete correspondence based on the generated information.

In this case, the object influence determination circuit 50 determines the degree of damage including at least one of pain, breakage, and perforation given to the object O.

Therefore, since the degree of damage to the object O can be known, it is possible to determine whether to interrupt or cancel the operation (return the operation) or to continue the operation.

Alternatively, the object influence determination circuit 50 may determine the degree of influence on the function of at least part of the object O.

Therefore, since the degree of influence on the object O can be known, it is possible to determine whether to interrupt or cancel the operation (return the operation) or to continue the operation. In addition, it is possible to determine whether to perform a predetermined treatment on the object O.

Alternatively, the object influence determination circuit 50 may determine the degree of deformation and movement of the portion of the object O to which the force is applied from the flexible tubular portion 12 and/or the periphery thereof.

Therefore, since the degree of deformation and movement of the part of the object O and/or the periphery thereof is known, it is possible to determine whether to interrupt or cancel the operation (return the operation) or to continue the operation.

In addition, the force estimation system 14 can further include an information presentation device serving as an information presentation unit that feeds back presentation information to the operator of the flexible tubular portion 12 based on the force information calculated by the force calculation circuit 48A.

Therefore, by providing the operator with the force information, it is possible for the operator to continue the safe operation, interrupt the problematic operation, recover from the problematic state, and the like.

Alternatively, the force estimation system 14 may further include an information presentation device serving as an information presentation unit that feeds back presentation information to the operator of the flexible tubular portion 12 based on the influence on the object O determined by the object influence determination circuit 50.

Therefore, by providing the operator with at least one of pieces of the information indicating the degree of influence on the object O, it is possible for the operator to continue the safe operation, interrupt the problematic operation, recover from the problematic state, and the like.

In addition, the force estimation system 14 may further include a driving feedback circuit serving as an information feedback unit that feeds back the force information calculated by the force calculation circuit 48A as driving information of a driving circuit serving as a driving unit that drives the insertion of the flexible tubular portion 12 by power.

Therefore, by providing the force information to the driving circuit, it is possible for the driving circuit to continue the safe driving (operation), interrupt the problematic driving (operation), recover from the problematic state, and the like.

Alternatively, the force estimation system 14 may further include a driving feedback circuit serving as an information feedback unit that feeds back the influence on the object O determined by the object influence determination circuit 50 as driving information of a driving circuit serving as a driving unit that drives the insertion of the flexible tubular portion 12 by power.

Therefore, by providing the driving circuit with at least one of pieces of the information indicating the degree of influence on the object O, it is possible for the driving circuit to continue the safe driving (operation), interrupt the problematic driving (operation), recover from the problematic state, and the like.

The force estimation system 14 may further include a memory circuit 54 serving as a memory unit that stores the calculated force information.

Therefore, the operation situation by the operator can be appropriately checked by storing the calculated force information. That is, the generation point of the force and the shape of the portion can be checked by storing the force information together with the position and the shape. In addition, it is possible to check whether there is a problem, review improvement in operation, consider the policy at the next operation, and so on.

Instead, the force estimation system 14 may further include a memory circuit 54 serving as a memory unit that stores the presentation information fed back to the operator.

Therefore, the operation situation by the operator can be appropriately checked by storing the presentation information generated based on the force information. That is, the generation point of the force and the shape of the portion can be checked by storing the position and the shape. In addition, it is possible to check whether there is a problem, review improvement in operation, consider the policy at the next operation, and so on.

Alternatively, the force estimation system 14 may further include a memory circuit 54 serving as a memory unit that stores the driving information fed back to the driving unit.

Therefore, the operation situation by the operator can be appropriately checked by storing the driving information generated based on the force information. That is, the generation point of the force and the shape of the portion can be checked by storing the position and the shape. In addition, it is possible to check whether there is a problem, review improvement in operation, consider the policy at the next operation, and so on.

In addition, the flexible tubular portion 12 is the endoscope insertion portion 12' of the endoscope or the small-diameter manipulator, which is inserted into the inside of the object O, and the force estimation system 14 can detect the force received from the object O in the inside of the object O.

At the time of insertion into the lumen of the patient who is the object O, treatment of the affected area of the object O, or the like by applying to the endoscope insertion portion 12' of the endoscope or the small-diameter manipulator, the burden on the patient can be reduced and the safe operation can be operated.

In particular, the small-diameter endoscope and the manipulator are required for operations within the patient's body. According to the present embodiment, it is possible to realize the small-diameter endoscope or the manipulator while enabling the safe operation.

In addition, the flexible tubular portion 12 is the endoscope insertion portion 12' of the large intestine endoscope, and the force estimation system 14 further estimates the force for inserting and removing the endoscope insertion portion 12' on the assumption that the resultant force of the force estimated to be applied to the endoscope insertion portion 12' inside the large intestine 112 is substantially balanced with the force for inserting and removing the endoscope insertion portion 12'.

Therefore, the force for insertion and removal can be obtained from only the coordinate and shape information of the endoscope insertion portion 12' of the large intestine endoscope.

Even if roughly calculated, since a rough force for insertion and removal can be obtained, the operation of the operator or the insertion manipulator can be grasped simply and quantitatively, which can lead to the prevention of applying an excessive force.

In addition, the flexible tubular portion 12 is the endoscope insertion portion 12' of the large intestine endoscope, and the force estimation system 14 further estimates the information about the force for inserting and removing the endoscope insertion portion 12' on the assumption that the resultant force of the force estimated to be applied to the endoscope insertion portion 12' inside the large intestine 112 and the insertion direction component of the endoscope insertion portion 12' near the anus 114 in the force for inserting and removing the endoscope insertion portion 12' are substantially balanced.

Therefore, the information about the force for insertion and removal can be obtained from only the coordinate and shape information of the endoscope insertion portion 12' of the large intestine endoscope.

Even if roughly calculated, since the information about a rough force for insertion and removal can be obtained, the operation of the operator or the insertion manipulator can be grasped simply and quantitatively, which can lead to the prevention of applying an excessive force.

In addition, as described above, the force information calculation method according to the present embodiment is the force information calculation method for calculating force information (position, direction, and/or magnitude of a force) about the forces applied to one or more positions of the flexible tubular portion 12 having flexibility. The force information calculation method includes a first step (for example, step S10A) of measuring or estimating the coordinates and shapes (information) (curvature, bending amount, bending angle, and the like) at the plurality of longitudinal positions of the flexible tubular portion 12, a second step (for example, step S12A) of obtaining bending moments at the plurality of positions from the shapes obtained in the first step and the prestored bending stiffness at the plurality of positions, and a third step (for example, step S14A) of calculating force information (position, direction, and/or magnitude of the force) about the forces applied to the one or more positions of the flexible tubular portion 12 from the coordinates of the plurality of positions obtained in the first step and the bending moments at the plurality of positions obtained in the second step.

In this manner, the external force causing the bending can be efficiently detected, without directly measuring the force, by detecting only the bending state and the coordinates.

When the flexible tubular portion 12 is inserted into the inside of the object O, the force information calculation method may further include a fourth step (for example, step S18A) of determining the influence on the object O that may occur due to the force information obtained in the third step.

As described above, the external force causing the bending is detected, without directly measuring the force, by detecting only the bending state and the coordinates. Furthermore, the influence on the object O can be determined efficiently and quantitatively based on the detected external force.

Second Embodiment

Next, a second embodiment of the present invention will be described. In the following, the same components as those of the first embodiment are denoted by the same reference numerals, and the description thereof will be omitted, and only parts different from the first embodiment will be described.

When the flexible tubular portion 12 and the force acting thereon cannot be simplified in two-dimension, three-dimensional processing is required to perform force detection. For example, there is a case where the flexible tubular portion 12 has a three-dimensional structure, and the flexible tubular portion 12 receives forces from various directions from the object O which do not fit in two-dimension.

Further, when the flexible tubular portion 12 cannot maintain its shape or posture by supporting its own weight, or when the magnitude of gravity cannot be ignored compared to the magnitude of the force received from the object O, it is necessary to determine the force information received by the flexible tubular portion 12, including the influence of gravity.

The present embodiment illustrates a case where the influence of gravity is divided from the influence of other forces to obtain force information.

It is possible to obtain force information even under the influence of gravity according to the gist of the present invention, without dividing the influence of gravity from the influence of other forces, but the influence of gravity is divided and processed so as to obtain more accurate information or information other than gravity.

Figure 25:
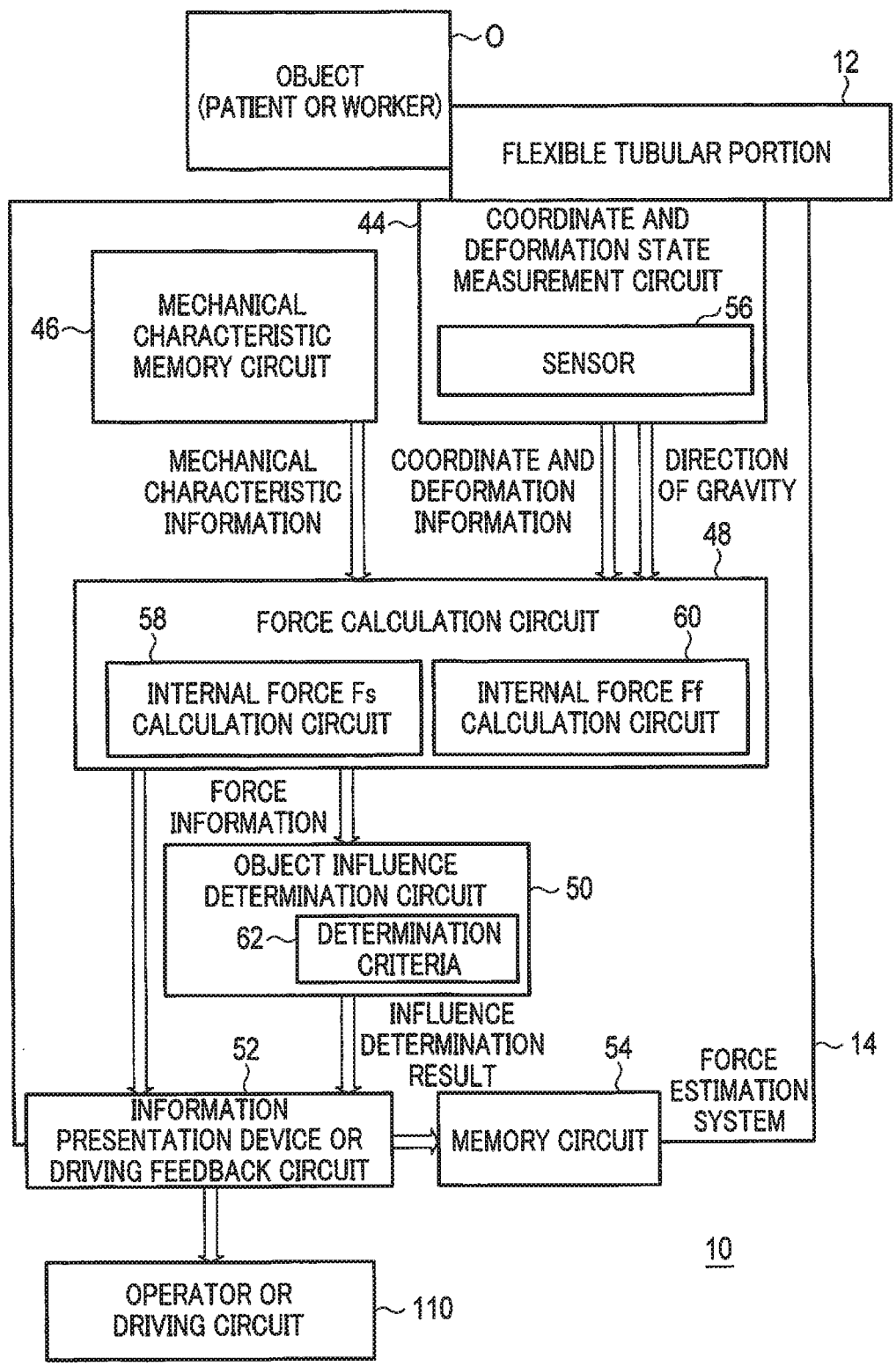
FIG. 25 is a block diagram illustrating an overall configuration example of a force estimation system according to a second embodiment of the present invention.

The force estimation system 10 according to the second embodiment of the present invention differs from the configuration of the first embodiment in the following points. That is, as illustrated in FIG. 25, a coordinate and deformation state measurement circuit 44 has a function of measuring the direction of gravity, and a mechanical characteristic memory circuit 46 also uses mass information of each segment of the flexible tubular portion 12 as mechanical characteristic information. When a force calculation circuit 48 performs calculation of an internal force Ff that is a second internal force, the mass information obtained at least from the mechanical characteristic memory circuit 46 and the information about the coordinates and the direction of gravity obtained from the deformation state measurement circuit 44 are used.

Figure 26:
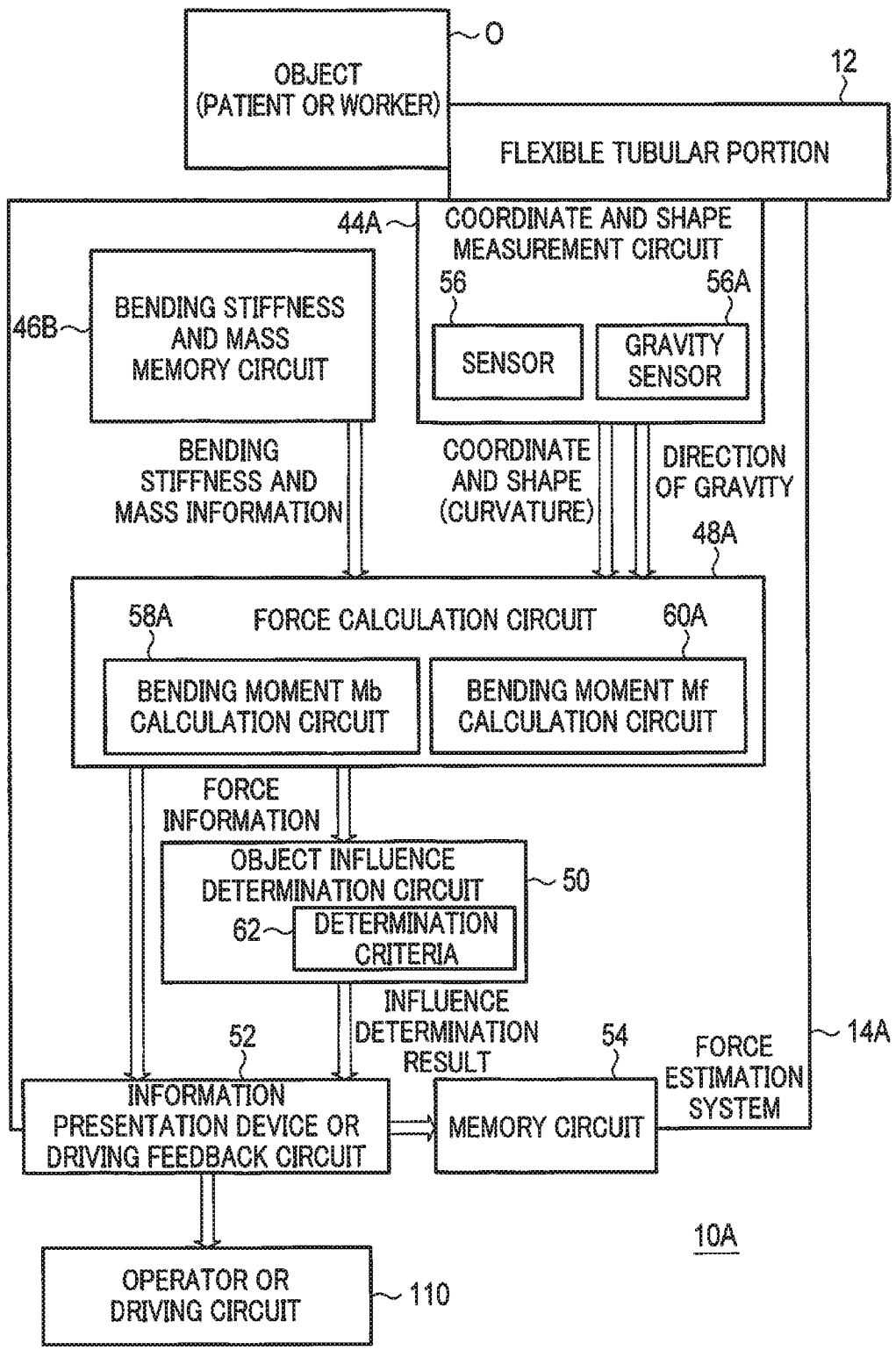
FIG. 26 is a block diagram illustrating a more specific overall configuration example of the force estimation system according to the second embodiment.

Similarly, a force estimation system 10A that calculates the force information based on the bending moment applied to the flexible tubular portion 12 differs from the configuration of the first embodiment in the following points. That is, as illustrated in FIG. 26, as the mechanical characteristic memory circuit 46, a bending stiffness and mass memory circuit 46B is provided instead of the bending stiffness memory circuit 46A in the first embodiment. When a force calculation circuit 48A performs calculation of a bending moment Mf that is a second bending moment, the mass information obtained from the bending stiffness and mass memory circuit 46B and the information about the direction of gravity obtained from the coordinate and shape measurement circuit 44A are used. The coordinate and deformation state measurement circuit 44 may include a gravity sensor 56A as a sensor, in addition to a sensor 56 such as a position sensor 64 or a shape sensor 66.

As described above, the force calculation circuit 48 or 48A can accurately obtain the influence of the gravity distributed to the flexible tubular portion 12 from the mass information and the direction of gravity, and can accurately obtain the force information received from the object O by the flexible tubular portion 12. In addition, as illustrated in FIG. 27, the force calculation circuit 48 or 48A may obtain the force information excluding the influence of gravity from the force received from the object O by the flexible tubular portion 12. Besides these, the obtained force information may change the combination of outputs, for example, simultaneously outputting three pieces of information, that is, the force information including the influence of gravity, the gravity information, and force information excluding the influence of gravity.

In addition, the information about the mass of each segment for determining the gravity (gravity distribution) in each segment may be stored in the mechanical characteristic memory circuit 46 or the bending stiffness and mass memory circuit 46B corresponding thereto, and the mass information may be stored in a memory circuit other than the mechanical characteristic memory circuit 46 or the bending stiffness and mass memory circuit 46B. It is apparent that this other memory circuit may also store mechanical characteristic information other than the mass information.

The force calculation circuit 48 or 48A obtains gravity information (gravity distribution) of each segment of the flexible tubular portion 12 by using the mass information obtained at least from the mechanical characteristic memory circuit 46 or the bending stiffness and mass memory circuit 46B and the information about the direction of gravity obtained from the coordinate and deformation state measurement circuit 44 or the coordinate and shape measurement circuit 44A. The force calculation circuit 48 or 48A uses the information about the direction of gravity when calculating the internal force Ff or the bending moment Mf.

Hereinafter, the measurement of the information about the direction of gravity and the calculation of the force information using the same will be described in detail.

[Detection of Information about Direction of Gravity]

The coordinate and deformation state measurement circuit 44 or the coordinate and shape measurement circuit 44A can obtain information about the direction of gravity in several ways.

[Gravity Sensor 56B]

One is the acquisition method using the gravity sensor 56A as illustrated in FIG. 26. In recent years, the gravity sensor has been miniaturized so as to be mounted on the smartphone, the tablet terminal, or the like, and the gravity sensor is easy to mount on the small-diameter bent member such as the endoscope 16.

The mounting position of the gravity sensor 56A on the endoscope 16 may be within a range in which the coordinates and the shape can be detected by the coordinate and deformation state measurement circuit 44 or the coordinate and shape measurement circuit 44A. The mounting position of the gravity sensor 56A may be the distal end or the middle portion of the flexible tubular portion 12. If the coordinates or the shape can be detected, although the mounting position of the gravity sensor 56A may not be necessarily the flexible tubular portion 12 itself, the mounting position of the gravity sensor 56A may be the peripheral portion adjacent to the flexible tubular portion 12. For example, in the case of the endoscope 16, as illustrated in FIG. 28, the peripheral portion adjacent to the flexible tubular portion 12 includes the operation portion 28 connected to the endoscope insertion portion 12' that is the flexible tubular portion 12.

Similar to the sensor 56 (the position sensor 64 and the shape sensor 66) described above in the first embodiment, the gravity sensor 56A may be incorporated in the flexible tubular portion 12 (endoscope insertion portion 12') or the periphery thereof, may be detachably attached, and may be mounted only when the direction of gravity is obtained.

[Sensor Arrangement and Setting for Determining Direction of Gravity]

Another method for acquiring information about the direction of gravity is to use the sensor 56 (the position sensor 64 and the shape sensor 66) that is incorporated in advance or detachably attached as described in the first embodiment. However, the sensor 56 is required to be arranged or set so that the direction of gravity is known.

Figure 29:
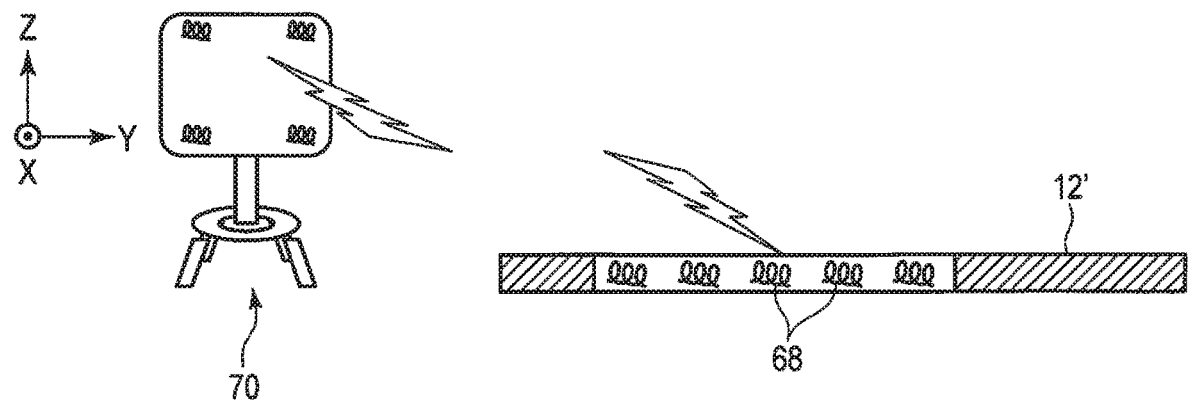
FIG. 29 is a view for explaining an antenna direction in the case of using a magnetic position sensor as a sensor that determines a direction of gravity.
Figure 30A:
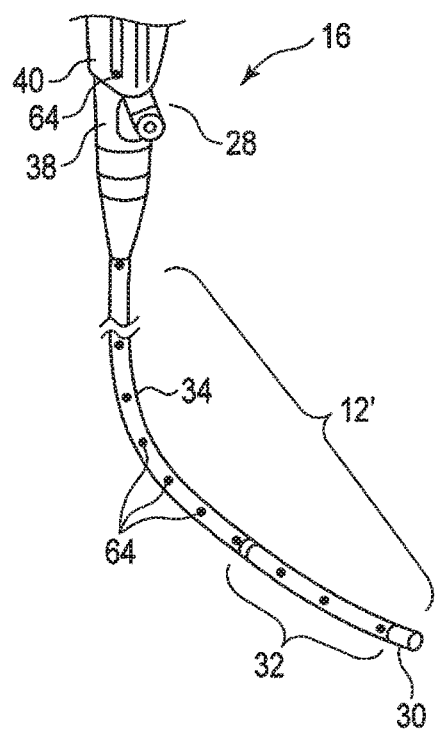
FIG. 30A is a view for explaining the arrangement of position sensors in the case of using the position sensors as a sensor that determines a direction of gravity.
Figure 30B:
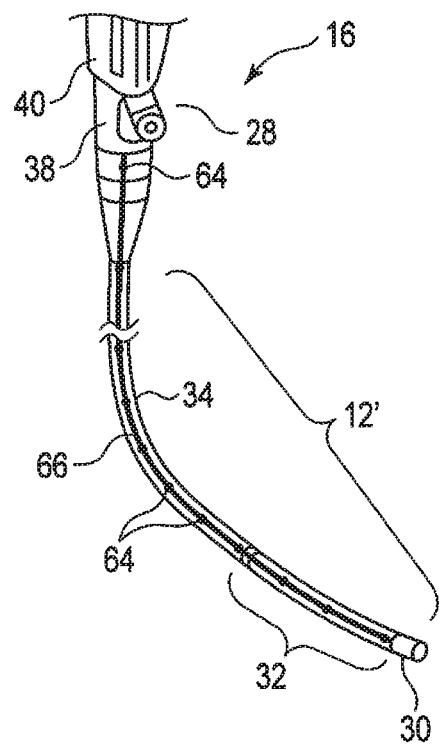
FIG. 30B is a view for explaining the arrangement of position sensors in the case of using the position sensors and shape sensors as a sensor that determines a direction of gravity.

For example, when a magnetic position sensor 64 is used, as illustrated in FIG. 29, a magnetic antenna 70 is disposed in a predetermined direction with respect to the direction of gravity, and the setting is reflected to the position information. As illustrated in FIG. 30A, in the endoscope 16 in which a plurality of position sensors 64 disposed so as to be distributed in the flexible tubular portion 12 (the endoscope insertion portion 12') are incorporated in the endoscope insertion portion 12', the position sensor 64 is further provided in the operation portion 28 connected to the endoscope insertion portion 12'. In this case, as illustrated in FIG. 30B, the shape sensor 66 may be further disposed along the longitudinal direction of the endoscope insertion portion 12'. With this configuration, in FIG. 29, for example, a negative Z-axis direction can be set as the gravity direction.

Furthermore, as illustrated in FIG. 3, only the shape sensor 66 may be provided in the endoscope insertion portion 12'. In this case, if the shape of the distal end can be detected from the operation portion 28, for example, if the operation portion 28 is fixed and arranged in a fixed direction, the direction of gravity can be detected based on the arrangement.

Therefore, based on the arrangement or setting of at least one of the position sensor 64 and the shape sensor 66, the direction of gravity at a plurality of positions can be measured.

[Force Calculation Circuits 48 and 48A]

The force calculation circuit 48 or 48A calculates the influence of gravity as follows.

Figure 31:
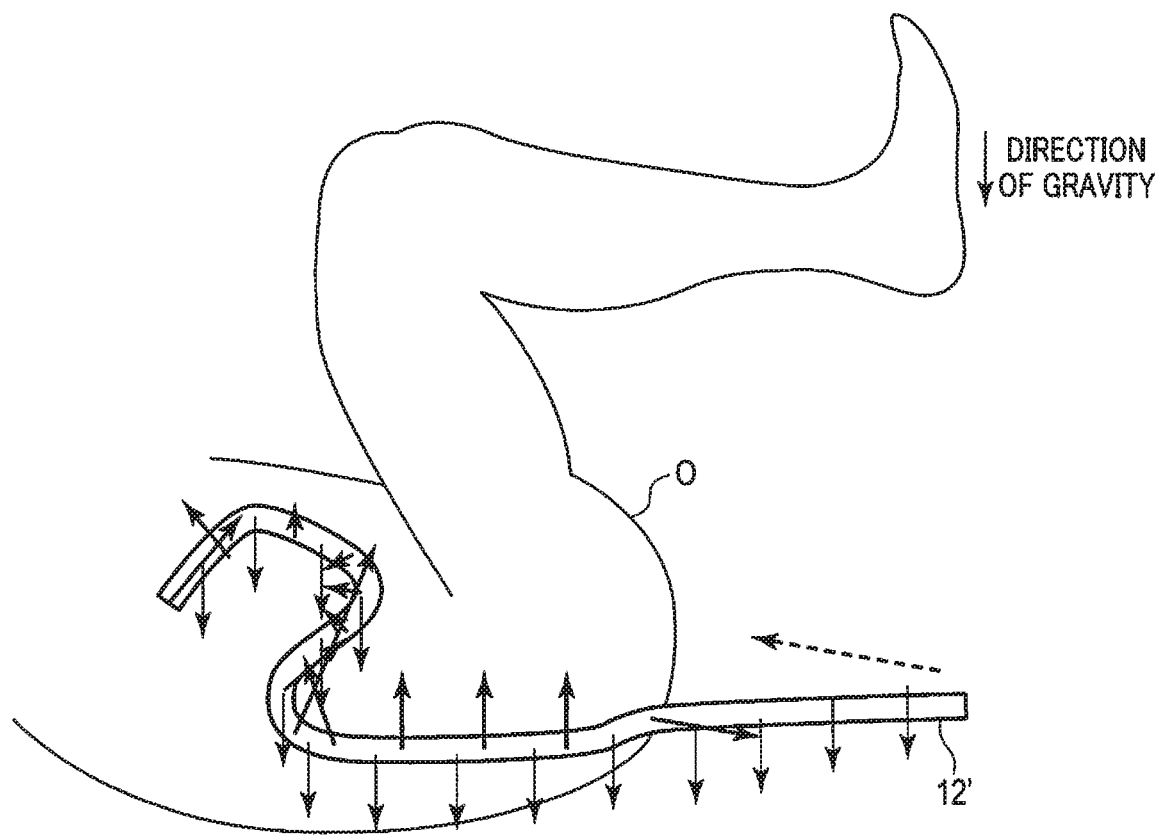
FIG. 31 is a view for explaining a force received by an endoscope insertion portion inserted into an object.

FIG. 31 illustrates a state in which the endoscope insertion portion 12' of the large intestine endoscope that is the flexible tubular portion 12 is inserted into the object O (patient). The gravity is assumed to work in the direction indicated by a thin arrow in the drawing. That is, the thin arrow drawn in the direction of gravity indicate the gravity applied to each segment.

In addition, thick arrows in the drawing indicate forces other than the gravity, which act on the endoscope insertion portion 12' in the large intestine that is the lumen. This is the force received from the large intestine by the endoscope insertion portion 12'. Even in the state in which unreasonable insertion is not performed, if the endoscope insertion portion 12' cannot support its own weight, the force to support the gravity applied to the endoscope insertion portion 12' is received from the large intestine.

The directions of the thin arrow and the thick arrows indicate the direction of the force, and the lengths thereof indicate the magnitude of the force.

The distribution of force to support the gravity is obtained as follows.

Figure 32:
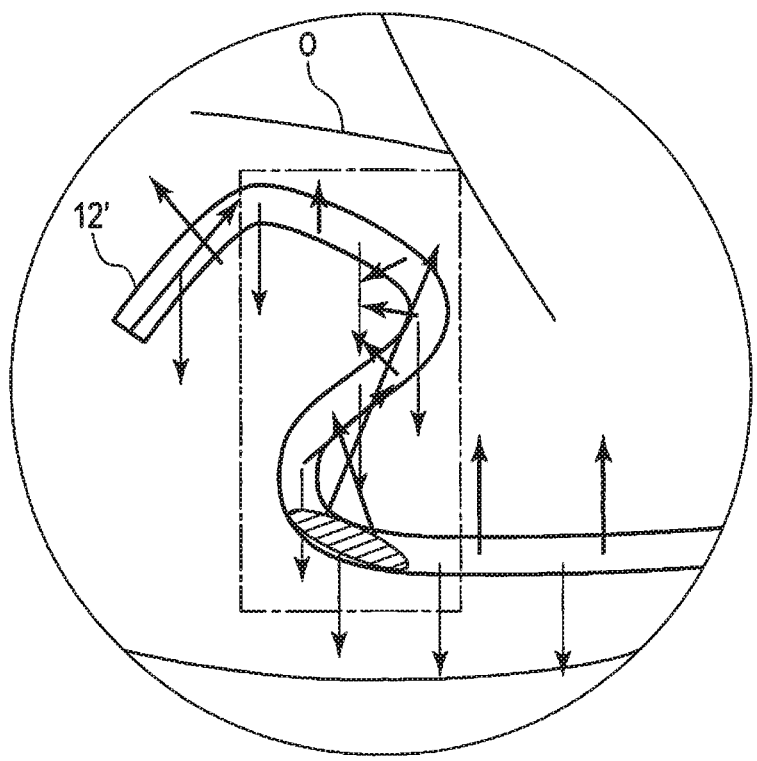
FIG. 32 is a partial enlarged view of FIG. 32 for explaining a force received by an endoscope insertion portion inserted into an object.

First, in the downwardly convex portion, it is assumed that the weight of the lower portion of the circumference, which is surrounded by a frame indicated by a dashed-dotted line in FIG. 32 that is a partial enlarged view of FIG. 31, is applied (therefore, the portion indicated by hatching in FIG. 32 has the largest applied force). In addition, when the shape of the downwardly convex portion is flatter than in the case of hanging, the force necessary to produce the flat state may be calculated. Similarly, when the shape of the upwardly convex portion is an acute angle, the force necessary to produce an acute angle state may be calculated by hanging. In this manner, it is possible to estimate the force that the endoscope insertion portion 12' holds so as not to hang down.

These estimation methods may be combined or estimated from the measurement results of the weight distribution of the human body or colon model.

In addition, even in the flexible tubular portion 12 having a plurality of joints such as a manipulator, the distribution of the force supporting the own weight can be estimated by performing the same estimation.

Therefore, the following can be achieved by estimating the distribution of the weight of the flexible tubular portion 12 and the distribution of the force (reaction force) that supports the weight.

The force applied to the flexible tubular portion 12 can be obtained more accurately.

Of the forces applied to the flexible tubular portion 12, the force other than the force (reaction force) that supports the gravity can be obtained. (Calculated as the difference between the force actually estimated to be applied and the reaction force against the gravity.)

The distribution of the force that supports the weight of the flexible tubular portion 12 can be estimated.

Due to this, it is possible to estimate the load applied to the organ by the weight of the flexible tubular portion 12 by insertion.

In addition, a dashed arrow in FIG. 31 indicates a force by which the operator such as the doctor inserts the endoscope insertion portion 12' that is the flexible tubular portion 12. Here, the direction of the dashed arrow represents the direction of the force, and the length of the dashed arrow represents the magnitude of the force.

Since the forces applied to the entire endoscope insertion portion 12', including the insertion force, are balanced, the insertion force amount or the direction can be obtained.

In FIG. 31, in the vicinity of the anus, in addition to the force received by the endoscope insertion portion 12' from the body and the force to balance with the gravity, part of the reaction force is added to the pushing force of the operator such as the doctor to thereby become a lateral force.

[Calculation Example in Case of Three-Dimension]

Figure 33:
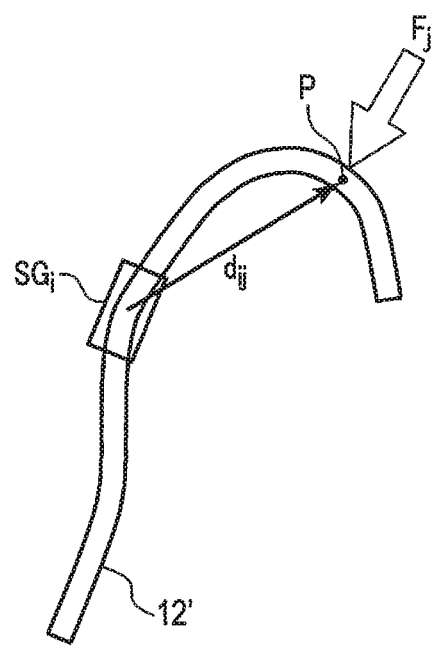
FIG. 33 is a view illustrating a j-th force $F_j$ acting on a certain point of an endoscope insertion portion and a vector $d_{ij}$ from a center of a segment $SG_i$ to a j-th action point.

Formula 4c and Formula 5b expressed for the case of the three-dimension described in the first embodiment will be described in more detail with reference to FIG. 33. FIG. 33 is a view for explaining a j-th force when a plurality of forces are applied to the endoscope insertion portion 12' that is the flexible tubular portion 12.

The j-th pressing force acting on a certain point of the endoscope insertion portion 12' is $F_j$, the direction vector from the i-th segment $SG_i$ to the application point of the j-th force is $d_{ij}$, and the second bending moment due to an external force, which is estimated to act on the segment $SG_i$ by a plurality of external forces, is $Mf_i$.

At this time, the following relationship is established between the vector $d_{ij}$, the pressing force $F_j$, and the second bending moment $Mf_i$ according to Formula 5b.

$$Mf_i = \Sigma(d_{ij} \times F_j)$$

However, when the pressing force $F_j$ is more proximal than the segment $SG_i$ of the endoscope insertion portion 12', it is calculated as $F_j=0$.

When the components of the vector $d_{ij}$ and the pressing force $F_j$ are defined by Formula 10 and Formula 11, the above formula becomes like Formula 12 below.

Definition:

$$F_j = (fx_j, fy_j, fz_j) \quad \text{(Formula 10)}$$

$$d_{ij} = (dx_{ij}, dy_{ij}, dz_{ij}) \quad \text{(Formula 11)}$$

$$Mf_i = \Sigma(dy_{ij} \cdot fz_j - dz_{ij} \cdot fy_j, dz_{ij} \cdot fx_j - dx_{ij} \cdot fz_j, dx_{ij} \cdot fy_j - dy_{ij} \cdot fx_j) \quad \text{(Formula 12)}$$

Since the second bending moment $Mf_i$ estimated to act on the segment $SG_i$ from this external force and the first bending moment $Mb_i$ estimated from the bent shape of the segment $SG_i$ are approximately the same, the relationship of Formula 6 is established. When the plurality of external forces act, the relationship as expressed in Formula 8 is established.

In addition, when the number of segments for which the bending moment is to be calculated is larger than the number of parameters of the external force to be obtained, external force information is obtained by using the optimization method as described above, for example, as in the example of Formula 7 or Formula 9.

At that time, in the formula "number of conditional expressions ($N_s$ or $3N_s$)=number of variables ($N_f \times N_c$)" or "number of conditional expressions ($N_s$ or $3N_s$)>number of variables ($N_f \times N_c$)" described above in the first embodiment, in the case of the three-dimension, the number of information contents $N_c$ to be obtained, which affects the number of variables, can be $N_c=3$ if there is no particular limitation, as in force magnitude 1 and direction 2 or force component 3.

[Calculation Example of Influence of Gravity]

In the example illustrated in FIGS. 31 and 32, when the movement of the endoscope insertion portion 12' is extremely slow and static analysis is possible, the influence of the gravity on each segment can be considered as follows.

Figure 34:
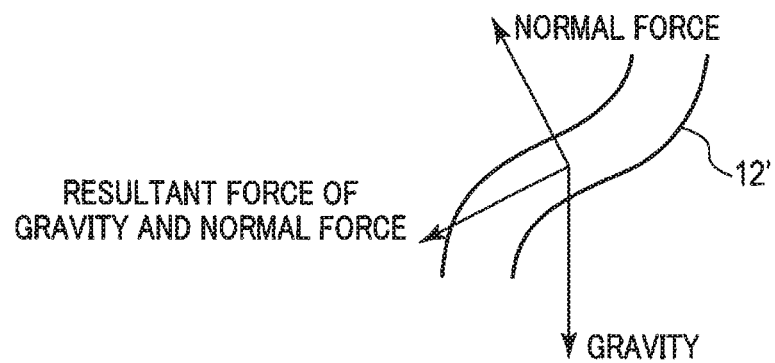
FIG. 34 is a view for explaining a force applied to each segment.

As one example, when there is the endoscope insertion portion 12' inside the object O and all the segments are in contact with the inside of the object O, each segment is considered to receive normal force from the inside of the object O in contact. At that time, the resultant force of the two forces of the gravity and the normal force applied to each segment becomes a force in the direction perpendicular to the contact surface as illustrated in FIG. 34. When the mass of the segment $SG_i$ is $ms_i$, the gravitational acceleration is g, and the angle between the segment $SG_i$ and the horizontal plane is $\theta_i$, the resultant force of the gravity and the normal force is $$ms_i \cdot g \cdot \sin \theta_i.$$

When all the forces in the direction perpendicular to the contact surface of each segment are added, it is considered that the component of the lateral force is canceled out or balanced with the amount of insertion and removal. On the other hand, the component of the force in the vertical direction is caught at a high place in the inside of the object O, or comes to be contained at a low place, and the gravity component is distributed and concentrated at these high and low places as illustrated in FIG. 35.

Figure 35:
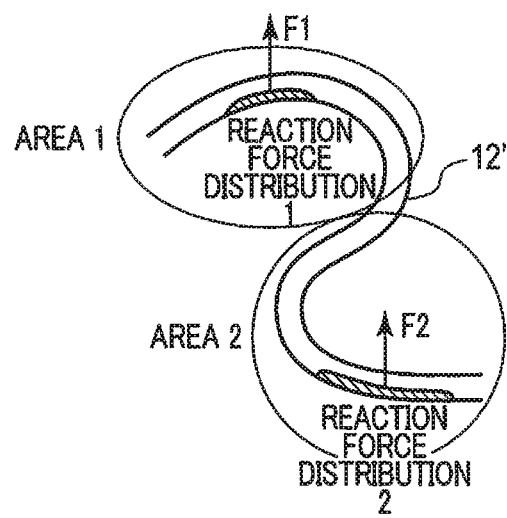
FIG. 35 is a view illustrating a resultant force and a reaction force distribution in a direction perpendicular to a contact surface where a segment is in contact with the inside of an object.

In FIG. 35, the resultant force F1 of the force in the direction perpendicular to the contact surface applied to the segment in the area 1 falls within the range of the reaction force distribution 1 indicated by hatching in the drawing, and similarly, the resultant force F2 of the force in the direction perpendicular to the contact surface applied to the segment in the area 2 falls within the range of the reaction force distribution 2. By doing so, although exact calculation may not be possible, the force calculation circuit 48 or 48A can roughly calculate the influence of the gravity on the flexible tubular portion 12.

Figure 36:
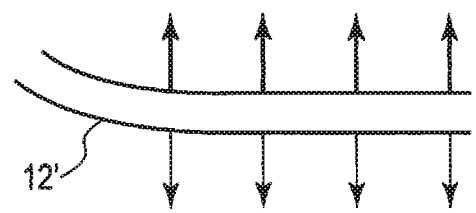
FIG. 36 is a view for explaining a force received by an endoscope insertion portion when the endoscope insertion portion is inserted into an object without almost any height difference.

In addition, particularly when there is almost no height difference, the gravity acts almost equally as illustrated in FIG. 36.

As another example, a case where there is the endoscope insertion portion 12' inside the object O and the endoscope insertion portion 12' is in contact with the inside of the object O near the highest position and the lowest position is considered. When applying this case to FIG. 35, the resultant force F1 of the gravity falls within the range of the reaction force distribution 1 in the segment in the area 1, and similarly, the resultant force F2 of the gravity applied to the segment in the area 2 falls within the range of the reaction force distribution 2. The force calculation circuit 48 or 48A can roughly calculate the influence of the gravity on the endoscope insertion portion 12'.

In addition, in a case where the endoscope insertion portion 12' is in contact with the inside of the object O only near the lowest position, in the example of FIG. 35, the force calculation circuit 48 or 48A can roughly calculate the influence of the gravity on the endoscope insertion portion 12' by assuming that the resultant force of the force of the gravity applied to the segments in area 1 and area 2 falls within the range of the reaction force distribution 2.

In this manner, by obtaining the influence of the gravity with respect to the flexible tubular portion 12 (endoscope insertion portion 12') and the reaction force from the object O or the like for supporting the gravity, the force calculation circuit 48 or 48A can accurately obtain the information about the force applied to the flexible tubular portion 12 or the information about the force applied to the flexible tubular portion 12 other than the gravity. Of these pieces of the information, which information is to be provided to the operator of the flexible tubular portion 12 can be determined appropriately, including any combination of them.

Modification

Figure 37:
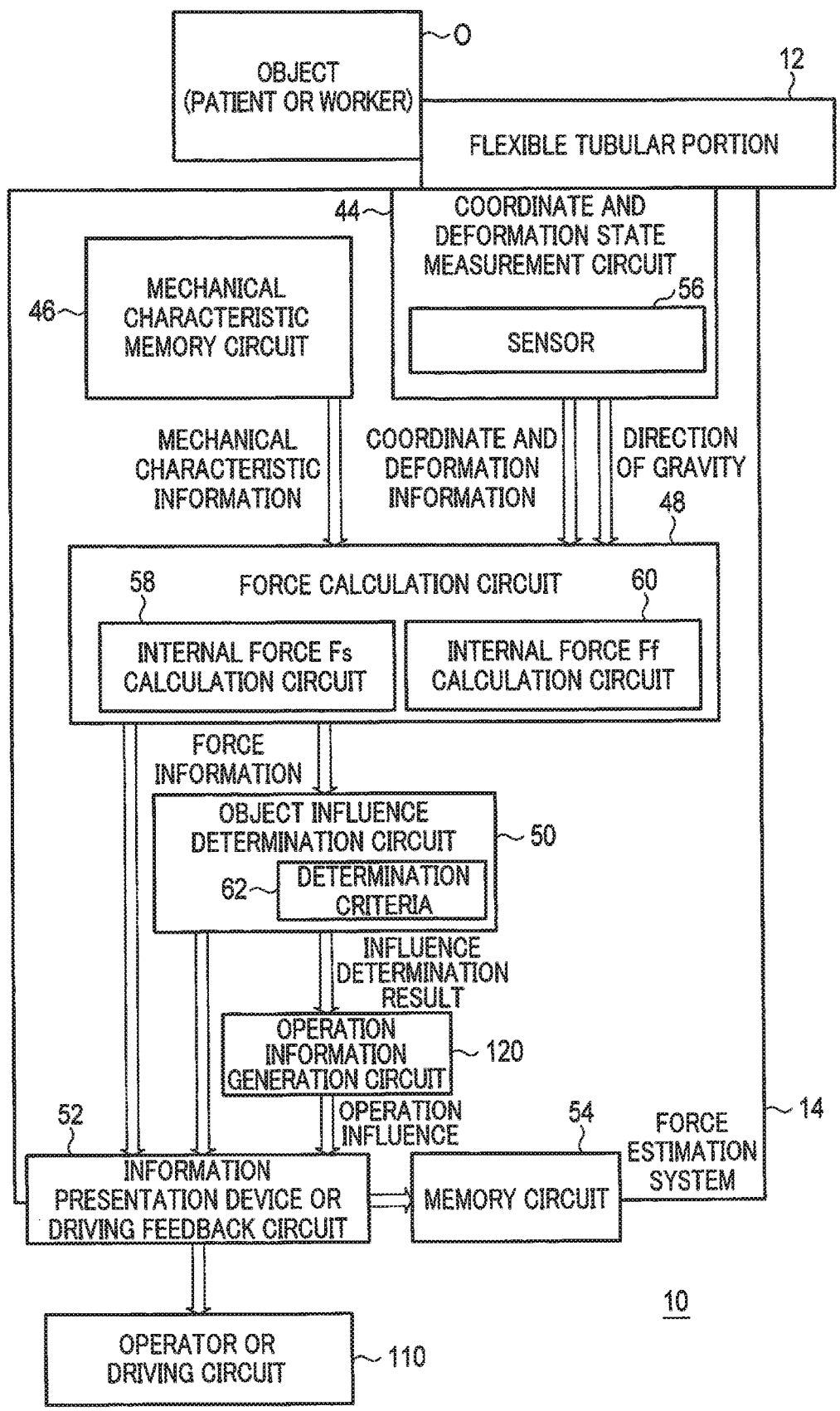
FIG. 37 is a block diagram illustrating an overall configuration example of a modification of a force estimation system according to the second embodiment.

FIG. 37 is a view illustrating a configuration of a modification of the force estimation system according to the second embodiment. The present modification includes an operation information generation circuit 120 that generates operation information based on an influence determination result from an object influence determination circuit 50.

As described in the first embodiment, the object influence determination circuit 50 can make the following determination.

The degree of damage given to the object O.

The influence on the function of at least part of the object O.

The degree of deformation and movement of part of the object O and/or the periphery thereof.

The operation information generation circuit 120 generates operation information of the flexible tubular portion 12, for example, information such as the operation method or the operation procedure of the endoscope insertion portion 12', and things to avoid and precautions, based on the influence information about the object O based on such force information, so as to avoid the influence on the object O or the influence determined to have the possibility of influence. In order to generate such information, operation information for each insertion condition and load condition of force can be generated appropriately by using a database or the like.

As a more specific example of the operation information, the following can be mentioned.

Stop/pull the insertion of the flexible tubular portion 12.

Since the flexible tubular portion 12 does not enter the inside of the object O only by the operation of pressing the flexible tubular portion 12, another operation method such as twisting and pressing is tried.

Posture conversion of the object O to a specific direction is not performed so that the influence of the weight of the flexible tubular portion 12 is not increased.

By generating such operation information as operation support information, it is possible to avoid the situation to be avoided in a specific way among the influence assumed based on quantitative force information.

Of course, the operation information generation circuit 120 as in this modification can be applied to the first embodiment as well.

As described above, the force estimation system 10 according to the second embodiment of the present invention can exhibit the same effects as those of the first embodiment.

Furthermore, in the force estimation system 10 according to the second embodiment, the force estimation system 14 serving as the force information calculation unit calculates the force information about the forces applied to the one or more positions of the flexible tubular portion 12 through an arithmetic operation by taking into account the influence of the gravity (longitudinal gravity distribution) at a plurality of longitudinal positions of the flexible tubular portion 12.

Therefore, the force information can be accurately obtained by taking into account the influence of the gravity.

In this case, the force estimation system 14 calculates the force information about the force other than the gravity (excluding the influence of the gravity) applied to the one or more positions of the flexible tubular portion 12 through an arithmetic operation.

Therefore, it is possible to obtain accurate force information, excluding the influence of the gravity.

In addition, the coordinate and deformation state measurement circuit 44 or the coordinate and shape measurement circuit 44A serving as the coordinate and shape measurement unit is further set to be able to specify the direction of the gravity with respect to the coordinates, or has a function. The mechanical characteristic memory circuit 46 or the bending stiffness and mass memory circuit 46B serving as the mechanical characteristic memory unit further has a function of storing the mass at the plurality of positions. The force calculation circuit 48 or 48A serving as the force calculation unit calculates the force information about the forces applied to the one or more positions of the flexible tubular portion 12 through an arithmetic operation by using the coordinates, the shape, the bending stiffness, and the direction of the gravity, and the gravity obtained from the mass at the plurality of positions.

Therefore, the influence of the gravity distributed to the flexible tubular portion 12 can be accurately obtained from the mass information and the direction of gravity, and the force information received from the object O by the flexible tubular portion 12 can be accurately obtained.

In this case, the coordinate and shape measurement circuit 44A further includes a gravity sensor 56A that is incorporated in a portion adjacent to the flexible tubular portion 12 that can measure the coordinates and shape of the portion including at least a portion of the flexible tubular portion 12 by the flexible tubular portion 12 or the coordinate and shape measurement circuit 44A, for example, the operation portion 28, or is detachably attached to the flexible tubular portion 12 or the portion adjacent to the flexible tubular portion 12. The direction of the gravity at the plurality of positions can be measured based on the output of the gravity sensor 56A and the coordinates and the shape at the plurality of positions measured by the coordinate and shape measurement circuit 44A.

Therefore, the direction of the gravity can be easily detected by using the gravity sensor.

Alternatively, the coordinate and shape measurement circuit 44A includes at least one of the position sensor 64 and the shape sensor 66, which are incorporated in the flexible tubular portion 12 or are detachably attached to the flexible tubular portion 12. The direction of the gravity at the plurality of positions can be measured based on the arrangement or setting of at least one of the position sensor 64 and the shape sensor 66.

Therefore, at least one of the position sensor 64 and the shape sensor 66 can be used to detect the direction of the gravity.

The object influence determination circuit 50 serving as the object influence determination unit can further include an operation information generation circuit 120 serving as an operation information generation unit that generates operation information (operation method, operation procedure, avoidance/precautions) of the flexible tubular portion 12 so as to avoid the influence on the object O or the influence determined to have the possibility of influence.

Therefore, it is possible to avoid the situation to be avoided in a specific way among the influence assumed based on quantitative force information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A force estimation system comprising:
 a processor configured to:
   calculate a first bending moment in each segment of a plurality of longitudinally divided segments of a flexible tubular portion, based on a deformation state and a mechanical property of the segment;

calculate a second bending moment generated for the segment of the plurality of longitudinally divided segments based on a vector of the forces applied to the flexible tubular portion and a vector from the segment to one or more positions of the flexible tubular portion; and calculate, through an arithmetic operation, force information regarding forces applied to the one or more positions of the flexible tubular portion based on the first bending moment and the second bending moment.

2. The force estimation system according to claim 1, wherein the processor is configured to calculate the force information regarding the forces applied to the one or more positions of the flexible tubular portion by taking into account influence of gravity at a plurality of longitudinal positions of the flexible tubular portion through the arithmetic operation.

3. The force estimation system according to claim 2, wherein the processor is configured to calculate the force information regarding the force other than gravity, which is applied to the one or more positions of the flexible tubular portion through the arithmetic operation.

4. The force estimation system according to claim 1, wherein the processor is configured to:
estimate, from the deformation state and the mechanical characteristic, a first internal force generated at the plurality of longitudinal positions of the flexible tubular portion and peripheries of the longitudinal positions;
estimate a second internal force that is generated at the plurality of longitudinal positions of the flexible tubular portion and the peripheries of the longitudinal positions by the forces applied to the one or more positions of the flexible tubular portion; and
calculate the force information regarding the forces applied to the one or more positions of the flexible tubular portion through the arithmetic operation based on a balance of the first internal force and the second internal force.

5. The force estimation system according to claim 1, wherein the processor is configured to:
estimate, from the deformation state and the mechanical characteristic, a first bending moment, generated at the plurality of longitudinal positions of the flexible tubular portion and peripheries of the longitudinal positions;
estimate, a second bending moment that is generated at the plurality of longitudinal positions of the flexible tubular portion and the peripheries of the longitudinal positions by the forces applied to the one or more positions of the flexible tubular portion; and
calculate the force information regarding the forces applied to the one or more positions of the flexible tubular portion through the arithmetic operation based on a balance between the first bending moment and the second bending moment.

6. The force estimation system according to claim 1, further comprising a memory configured to store bending stiffness at the plurality of longitudinally divided segments,
wherein the processor is configured to measure or estimate coordinates and shapes at the plurality of longitudinally divided segments as the deformation states at the plurality of longitudinally divided segments of the flexible tubular portion, and wherein the force information regarding the forces applied to the one or more positions of the flexible tubular portion is calculated by using the coordinates, the shapes, and the bending stiffness at the plurality of longitudinally divided segments through the arithmetic operation.

7. The force estimation system according to claim 6, further comprising at least one of a position sensor and a shape sensor,
wherein the position sensor and the shape sensor are arranged in the flexible tubular portion or a portion adjacent to the flexible tubular portion, or are detachably attached to the flexible tubular portion or the portion adjacent to the flexible tubular portion, and
wherein the processor is configured to measure the coordinates and the shapes at the plurality of positions based on an output of the at least one of the position sensor and the shape sensor.

8. The force estimation system according to claim 7, wherein the processor is configured to measure the coordinates and the shapes at the plurality of positions by performing estimation in addition to processing of a value of the output of the at least one of the position sensor and the shape sensor.

9. The force estimation system according to claim 6, wherein the memory is configured to store information on mass at the plurality of longitudinally divided segments of the flexible tubular portion, and
wherein the processor is configured to:
specify a direction of gravity with respect to the coordinates; and
calculate the force information regarding the forces applied to the one or more positions of the flexible tubular portion by using the coordinates, the shapes, the bending stiffness, the direction of the gravity, and the gravity obtained from the mass at the plurality of longitudinally divided segments through the arithmetic operation.

10. The force estimation system according to claim 9, further comprising a gravity sensor arranged in a portion adjacent to the flexible tubular portion, the gravity sensor being configured to measure coordinates and a shape of a portion including at least part of the flexible tubular portion, or is detachably attached to the flexible tubular portion or the portion adjacent to the flexible tubular portion, and
wherein the direction of the gravity at the plurality of longitudinally divided segments is measurable based on an output of the gravity sensor and the coordinates and the shapes at the plurality of longitudinally divided segments measured.

11. The force estimation system according to claim 9, further comprising at least one of a position sensor and a shape sensor, which are arranged in the flexible tubular portion or are detachably attached to the flexible tubular portion, and
wherein the processor is configured to measure the direction of the gravity at the plurality of longitudinally divided segments based on an arrangement and setting of at least one of the position sensor and the shape sensor.

12. The force estimation system according to claim 6, wherein the processor is configured to:
calculate a curvature at each segment of the plurality of longitudinally divided segments from the shape information at the plurality of longitudinally divided segments;

calculate the first bending moments at the plurality of longitudinally divided segments from the curvature and the bending stiffness; and calculate the second bending moments at the plurality of longitudinally divided segments, from the forces applied to the one or more segments of the flexible tubular portion, and wherein the force information applied to the one or more positions of the flexible tubular portion is calculated based on the fact that the second bending moment and the first bending moment substantially coincide with each other at the plurality of positions.

13. The force estimation system according to claim 12, wherein, when a number of formulae derived from the balance between the first bending moment and the second bending moment at the plurality of positions is larger than a number of variables of the force information calculated by the processor, the processor is configured to calculate the force information by using an optimization method for minimizing an evaluation formula.

14. The force estimation system according to claim 13, wherein there are plural positions of the one or more positions of the flexible tubular portion, and wherein the processor is configured to calculate the force information in an order from a position on a distal end side of the flexible tubular portion among the plurality of positions of the flexible tubular portion.

15. The force estimation system according to claim 6, wherein the processor is configured to calculate the force information by applying a force actually applied to the flexible tubular portion to a simplified model to reduce an amount of calculation processing by the processor.

16. The force estimation system according to claim 15, wherein, when the force applied to the flexible tubular portion is a load distribution force, the processor is configured to apply the load distribution force to the simplified model of the force being applied to a finite point of the flexible tubular portion, and perform the calculation of the force information.

17. The force estimation system according to claim 15, wherein, when plural forces are applied to the flexible tubular portion, the processor is configured to calculate the force information by applying to the simplified model in which the flexible tubular portion and the position and the direction in which the actually applied force acts are on one plane.

18. The force estimation system according to claim 15, wherein the processor is configured to perform the calculation of the force information by applying to the simplified model in which the direction of the force applied to the flexible tubular portion is substantially perpendicular to the flexible tubular portion.

19. The force estimation system according to claim 6, wherein the flexible tubular portion is configured to be inserted into an object, and wherein the processor is configured to determine an influence on the object based on the force information.

20. The force estimation system according to claim 19, wherein the processor is configured to determine a degree of damage including at least one of pain, breakage, and perforation given to the object based on a determination criteria stored in the memory as the influence of the force information on the object, the determination criteria being related to the degree of damage including at least one of pain, breakage, and perforation given to the object.

21. The force estimation system according to claim 19, wherein the processor is configured to determine a degree of influence on a function of at least part of the object based on a determination criteria stored in the memory as the influence of the force information on the object, the determination criteria related to the degree of influence given to the function of the at least part of the object.

22. The force estimation system according to claim 19, wherein the processor is configured to determine a degree of deformation and movement of a portion of the object to which the force is applied from the flexible tubular portion and/or a periphery of the portion based on a determination criteria stored in the memory as the influence of the force information on the object, the determination criteria related to the degree of deformation and movement of the portion of the object to which the force is applied from the flexible tubular portion and/or the periphery of the portion.

23. The force estimation system according to claim 19, further comprising a driving circuit configured to drive the insertion of the flexible tubular portion by power, wherein the processor is configured to feed back the determined influence on the object as driving information of the driving circuit.

24. The force estimation system according to claim 19, wherein the processor is configured to generate operation information of the flexible tubular portion so as to avoid influence on the object.

25. The force estimation system according to claim 19, wherein the processor is configured to calculate the force information based on the first bending moment and the second bending moment substantially coinciding with each other in each of the segments.

26. The force estimation system according to claim 6, wherein the processor is configured to feed back presentation information to an operator of the flexible tubular portion based on the calculated force information.

27. The force estimation system according to claim 6, further comprising a driving circuit configured to drive the insertion of the flexible tubular portion by power, wherein the processor is configured to feed back the calculated force information as driving information of the driving circuit.

28. The force estimation system according to claim 1, wherein the processor further comprises a memory configured to store the calculated force information.

29. The force estimation system according to claim 1, wherein the flexible tubular portion is an insertion portion of an endoscope or a small-diameter manipulator, which is configured to be inserted into an object, and wherein the processor is configured to detect a force received by the flexible tubular portion from the object in the inside of the object.

30. The force estimation system according to claim 1, wherein the flexible tubular portion is an insertion portion of a large intestine endoscope, and wherein the processor is configured to estimate a force for inserting and removing the insertion portion on the assumption that a resultant force of a force estimated to be applied to the insertion portion inside a large intestine is substantially balanced with the force for inserting and removing the insertion portion, whereby the force for inserting and removing the insertion portion is obtained from only coordinate and shape information of the insertion portion.

31. The force estimation system according to claim 1,
wherein the flexible tubular portion is an insertion portion of a large intestine endoscope, and
wherein the processor is configured to estimate information regarding a force for inserting and removing the insertion portion on the assumption that a resultant force of a force estimated to be applied to the endoscope insertion portion inside a large intestine and an insertion direction component of the insertion portion near an anus of the force for inserting and removing the insertion portion are substantially balanced, whereby the information regarding the force for inserting and removing the insertion portion is obtained from only coordinate and shape information of the insertion portion.

32. A force estimation system for calculating force information regarding forces applied to one or more positions of a flexible tubular portion having flexibility through an arithmetic operation, the force estimation system comprising:
a processor configured to input the deformation state and the mechanical property at a plurality of longitudinal positions of the flexible tubular portion, and calculate the force information of the force applied to the individual positions of the flexible tubular portion based on the deformed state and the mechanical property,
wherein the processor is configured to calculate the force information regarding the forces applied to the one or more positions of the flexible tubular portion by taking into account influence of gravity at a plurality of longitudinal positions of the flexible tubular portion through the arithmetic operation.

33. A force estimation system for calculating force information regarding forces applied to one or more positions of a flexible tubular portion having flexibility through an arithmetic operation, the force estimation system comprising:
a processor configured to input the deformation state and the mechanical property at a plurality of longitudinal positions of the flexible tubular portion, and calculate the force information of the force applied to the individual positions of the flexible tubular portion based on the deformed state and the mechanical property,
wherein the flexible tubular portion is an insertion portion of a large intestine endoscope, and
wherein the processor is configured to estimate a force for inserting and removing the insertion portion on the assumption that a resultant force of a force estimated to be applied to the insertion portion inside a large intestine is substantially balanced with the force for inserting and removing the insertion portion, whereby the force for inserting and removing the insertion portion is obtained from only coordinate and shape information of the insertion portion.

34. A force estimation system for calculating force information regarding forces applied to one or more positions of a flexible tubular portion having flexibility through an arithmetic operation, the force estimation system comprising:
a processor configured to input the deformation state and the mechanical property at a plurality of longitudinal positions of the flexible tubular portion, and calculate the force information of the force applied to the individual positions of the flexible tubular portion based on the deformed state and the mechanical property,
wherein the flexible tubular portion is an insertion portion of a large intestine endoscope, and
wherein the processor is configured to estimate information regarding a force for inserting and removing the insertion portion on the assumption that a resultant force of a force estimated to be applied to the endoscope insertion portion inside a large intestine and an insertion direction component of the insertion portion near an anus of the force for inserting and removing the insertion portion are substantially balanced, whereby the information regarding the force for inserting and removing the insertion portion is obtained from only coordinate and shape information of the insertion portion.

* * * * *